(12) United States Patent
Anderson

(10) Patent No.: US 9,550,186 B2
(45) Date of Patent: Jan. 24, 2017

(54) MICRO-FLUIDIC PARTITIONING BETWEEN POLYMERIC SHEETS FOR CHEMICAL AMPLIFICATION AND PROCESSING

(71) Applicant: Brian L. Anderson, Lodi, CA (US)

(72) Inventor: Brian L. Anderson, Lodi, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 21 days.

(21) Appl. No.: 14/695,968

(22) Filed: Apr. 24, 2015

(65) Prior Publication Data

US 2015/0224504 A1    Aug. 13, 2015

Related U.S. Application Data

(62) Division of application No. 13/480,274, filed on May 24, 2012, now Pat. No. 9,038,689.

(60) Provisional application No. 61/490,406, filed on May 26, 2011.

(51) Int. Cl.

| | |
|---|---|
| *B01L 7/00* | (2006.01) |
| *C12Q 1/68* | (2006.01) |
| *B32B 37/00* | (2006.01) |
| *B32B 37/10* | (2006.01) |
| *B32B 37/18* | (2006.01) |
| *B32B 38/00* | (2006.01) |
| *B65B 9/02* | (2006.01) |

(52) U.S. Cl.
CPC .............. *B01L 7/52* (2013.01); *B32B 37/0038* (2013.01); *B32B 37/1027* (2013.01); *B32B 37/182* (2013.01); *B32B 38/0008* (2013.01); *C12Q 1/6806* (2013.01); *B65B 9/023* (2013.01); *Y10T 156/1741* (2015.01)

(58) Field of Classification Search
CPC . B65B 9/023; C12Q 1/6806; C12Q 2521/101; Y10T 156/1741; B32B 37/182; B32B 38/0008; B32B 37/0038; B32B 37/1027; B01L 7/52
See application file for complete search history.

(56) References Cited

U.S. PATENT DOCUMENTS

| | | | |
|---|---|---|---|
| 6,207,925 B1 * | 3/2001 | Kendall | B23K 26/067 219/121.63 |
| 6,761,016 B1 | 7/2004 | Soleri | |
| 7,041,481 B2 | 5/2006 | Anderson et al. | |
| 7,601,286 B2 | 10/2009 | Benett et al. | |
| RE41,780 E | 9/2010 | Anderson et al. | |

(Continued)

*Primary Examiner* — Jacob T Minskey
*Assistant Examiner* — Vishal I Patel
(74) *Attorney, Agent, or Firm* — Eddie E. Scott

(57) ABSTRACT

A system for fluid partitioning for chemical amplification or other chemical processing or separations of a sample, comprising a first dispenser of a first polymeric sheet, wherein the first polymeric sheet contains chambers; a second dispenser of a second polymeric sheet wherein the first dispenser and the second dispenser are positioned so that the first polymeric sheet and the second polymeric sheet become parallel; a dispenser of the fluid positioned to dispense the fluid between the first polymeric sheet and the second polymeric sheet; and a seal unit that seals the first polymeric sheet and the second polymeric sheet together thereby sealing the sample between the first polymeric sheet and the second polymeric sheet and partitioning the fluid for chemical amplification or other chemical processing or separations.

3 Claims, 18 Drawing Sheets

(56) References Cited

U.S. PATENT DOCUMENTS

| | | |
|---|---|---|
| 7,815,868 B1 | 10/2010 | Jones et al. |
| 7,837,946 B2 | 11/2010 | McBride et al. |
| 2003/0213552 A1* | 11/2003 | Chen .................. B23K 26/0732 156/272.8 |
| 2005/0022476 A1* | 2/2005 | Hamer .................... B29C 65/18 53/450 |
| 2008/0250753 A1 | 10/2008 | Sperry et al. |

* cited by examiner

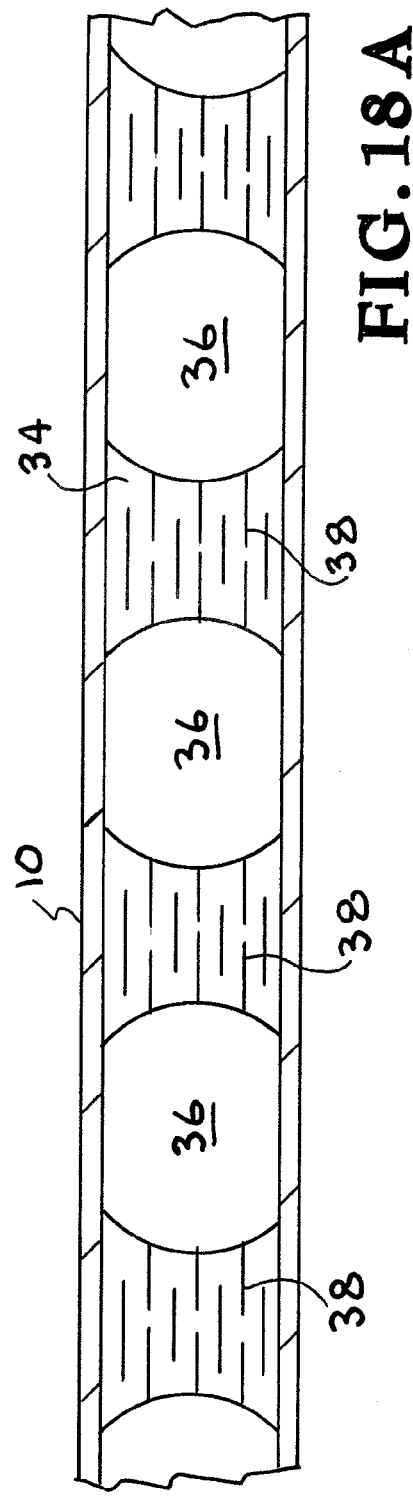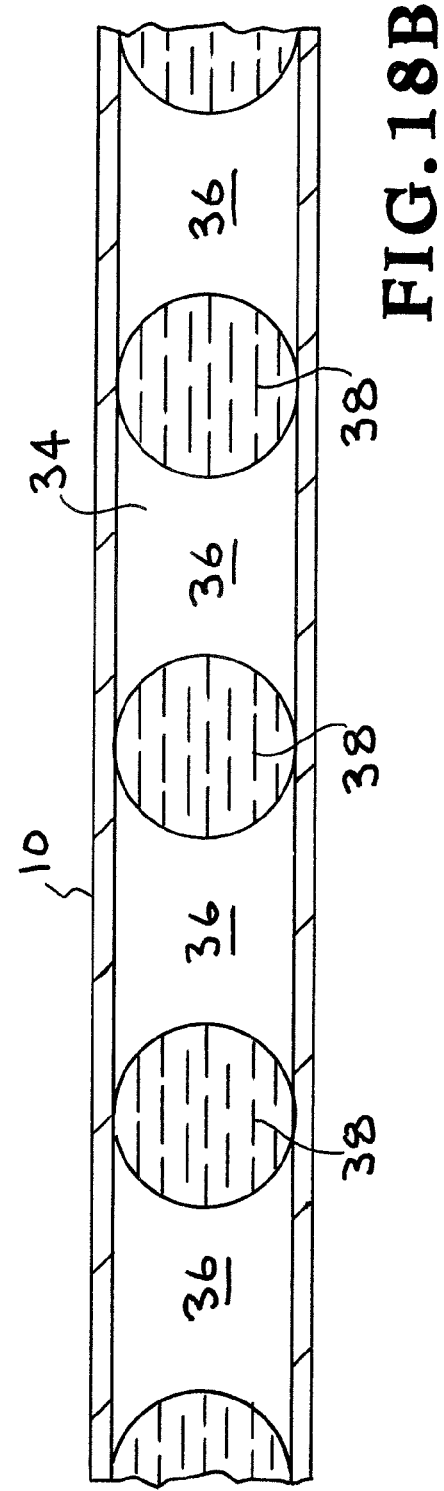

MICRO-FLUIDIC PARTITIONING BETWEEN POLYMERIC SHEETS FOR CHEMICAL AMPLIFICATION AND PROCESSING

CROSS-REFERENCE TO RELATED APPLICATIONS

The present application is a Division of application Ser. No. 13/480,274 filed May 24, 2012, which claims benefit under 35 U.S.C. §119(e) of U. S. Provisional Patent Application No. 61/490,406 filed May 26, 2011 entitled "Micro-Fluidic Partitioning Between Polymeric Sheets for Chemical Amplification and Processing," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present invention relates to chemical amplification and more particularly to for fluid partitioning between polymeric sheets for purposes of chemical amplification, such as Polymerase Chain Reaction (PCR)-based DNA (or RNA) detection, or for other chemical processing/separations.

State of Technology

Since the development by Kary Mullis of the PCR technique for amplification of DNA strands in 1983 for which he received the Nobel Prize for Chemistry in 1993, the chemistry and equipment for PCR have advanced dramatically. Amplification of DNA can be achieved starting from a single strand. In 1987, a joint venture between Perkin-Elmer and Cetus introduced Taq polymerase, a DNA polymerase that is stable through many rounds of thermal cycling. Starting around 1996, with the advent of fluorescent probes, real-time PCR methods have been employed where the amplification of DNA can be monitored as it occurs with optical detection techniques.

PCR is commonly carried out in a reaction volume of 10-200 µl in small reaction tubes (0.2-0.5 ml volumes) in a thermal cycler. Using this typical approach, PCR consists of a series of 20-40 repeated temperature cycles. Efficiencies have been gained by using arrays of reaction sites, for example arrays of 96 wells on a plate, and techniques for faster heating and cooling of the samples. Although initial efforts at DNA detection required hours to days, these fluorophore-based techniques using arrays of relatively small reaction sites have reduced the time-to-detection to less than one-hour.

More recently, additional time-to-detection advances have been achieved for detection of DNA, which have been demonstrated to be particularly useful for very dilute DNA solutions. When the initial DNA sample is very dilute, partitioning the sample into many separate aliquots can effectively increase the DNA to volume ratio for the fluid partitions that contain DNA, can decrease the number of thermal cycles necessary to reach the minimum fluorescent probe detection limit, and thereby decrease the detection time. Several methods have been employed for this fluid partitioning, including micro-well plates, and arrays of reaction sites and flow channels formed into various substrates. Most of these fluid partitioning approaches have reaction volumes on the order of a micro-liter (µl) and were discrete plates or other batch reaction array approaches. However, some effort has been made to reduce the volume of reaction sites toward the nano-liter range using arrays of very small capillaries, reaction sites on chips, or other droplet techniques.

The most promising recent advance, which not only significantly reduces the sample volume, but can also be implemented as a continuous process providing absolute quantification, is the suspension of micro-liter (i.e., $10^{-6}$ liter) to pico-liter (i.e., $10^{-12}$ liter) sized droplets in an immiscible carrier fluid. This approach may also be extended to include emulsions or gels. Lawrence Livermore National Laboratory, Quantalife™, and RainDance Technologies™ have developed approaches that involve very small droplets in an immiscible fluid. Quantalife™ has demonstrated the ability to generate mono-disperse nanoliter (i.e. $10^{-9}$ liter) sized droplets, perform the thermo-cycling in a conventional 96 well cycler with 20,000 droplet per well, and then use a flow system for detection of individual droplets in series at a rate of 32 wells/hr or 640,000 droplets/hr.

The present invention provides the same advantages as the approach of suspending droplets in an immiscible fluid, including (1) absolute quantification, (2) very small sample size resulting in reduced detection times, and (3) potential for continuous operation for increased throughput, but also includes the additional advantages of (1) providing a robust flexible framework for the partitioned samples that allow more directing handling and facilitates processing in automated equipment, (2) eliminating the need for an immiscible fluid thereby decreasing the time for heating and cooling and the resultant reduction in time to detection, and (3) allowing simultaneous detection of many samples in a row or array, again reducing detection time.

In addition to being applicable for DNA amplification and detection process using thermal cyclers and optical detection, the invention described herein is applicable to isothermal amplification processes and other DNA detection methods.

U.S. Pat. No. 7,041,481 issued May 9, 2006 to Brian L. Anderson, Billy W. Colston, Jr., and Chris Elkin and U.S. Pat. No. RE 41,780 for Chemical amplification based on fluid partitioning contains the state of technology information reproduced below. U.S. Pat. No. 7,041,481 and U.S. Pat. No. RE 41,780 are incorporated herein by this reference for all purposes.

The polymerase chain reaction (PCR), is a cyclic process whereby a large quantity of identical DNA strands can be produced from one original template. The procedure was developed in 1985 by Kary Mullis, who was awarded the 1993 Nobel Prize in chemistry for his work. In PCR, DNA is immersed in a solution containing the enzyme DNA polymerase, unattached nucleotide bases, and primers, which are short sequences of nucleotides designed to bind with an end of the desired DNA segment. Two primers are used in the process: one primer binds at one end of the desired segment on one of the two paired DNA strands, and the other primer binds at the opposite end on the other strand. The solution is heated to break the bonds between the strands of the DNA, then when the solution cools, the primers bind to the separated strands, and DNA polymerase quickly builds a new strand by joining the free nucleotide bases to the primers in the 5'-3' direction. When this process is repeated, a strand that was formed with one primer binds to the other primer, resulting in a new strand that is restricted solely to the desired segment. Thus the region of DNA between the primers is selectively replicated. Further repetitions of the process can produce a geometric increase in the number of copies, (theoretically 2 n if 100% efficient whereby n equals the number of cycles), in effect billions of copies of a small piece of DNA can be replicated in several hours.

A PCR reaction is comprised of (a) a double-stranded DNA molecule, which is the "template" that contains the sequence to be amplified, (b) primer(s), which is a single-stranded DNA molecule that can anneal (bind) to a complimentary DNA sequence in the template DNA; (c) dNTPs, which is a mixture of dATP, dTTP, dGTP, and dCTP which are the nucleotide subunits that will be put together to form new DNA molecules in the PCR amplification procedure; and (d) Taq DNA polymerase, the enzyme which synthesizes the new DNA molecules using dNTPs.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a method for fluid partitioning between polymeric sheets for purposes of chemical amplification, such as Polymerase Chain Reaction (PCR)-based DNA (or RNA) detection, or for other chemical processing/separations. In some embodiments of the present invention these partitioned fluid "packets" generally have volumes between one micro-liter and one pico-liter. In other embodiments of the present invention, such as chemical separations and/or processing, or cell culture, these partitioned fluid "packets" can have volumes of micro-liters to milli-liters. The fluid to be partition is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA identification. Applications for such fluid partitioning include, but are not limited to, rapid DNA detection, enhanced drug discovery, rapid pathogen detection, and rapid multiplexed simultaneous detection of multiple DNA strands. Other downstream applications include DNA/RNA/gene sequencing as well as personalized therapy evaluations.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 18A AND FIG. 18B illustrates an embodiment of the present invention providing a method of sealing fluid partitions using longitudinal cavities between the layers and creating micro-reactors by batch processing.

DETAILED DESCRIPTION OF SPECIFIC EMBODIMENTS

Figure 1:
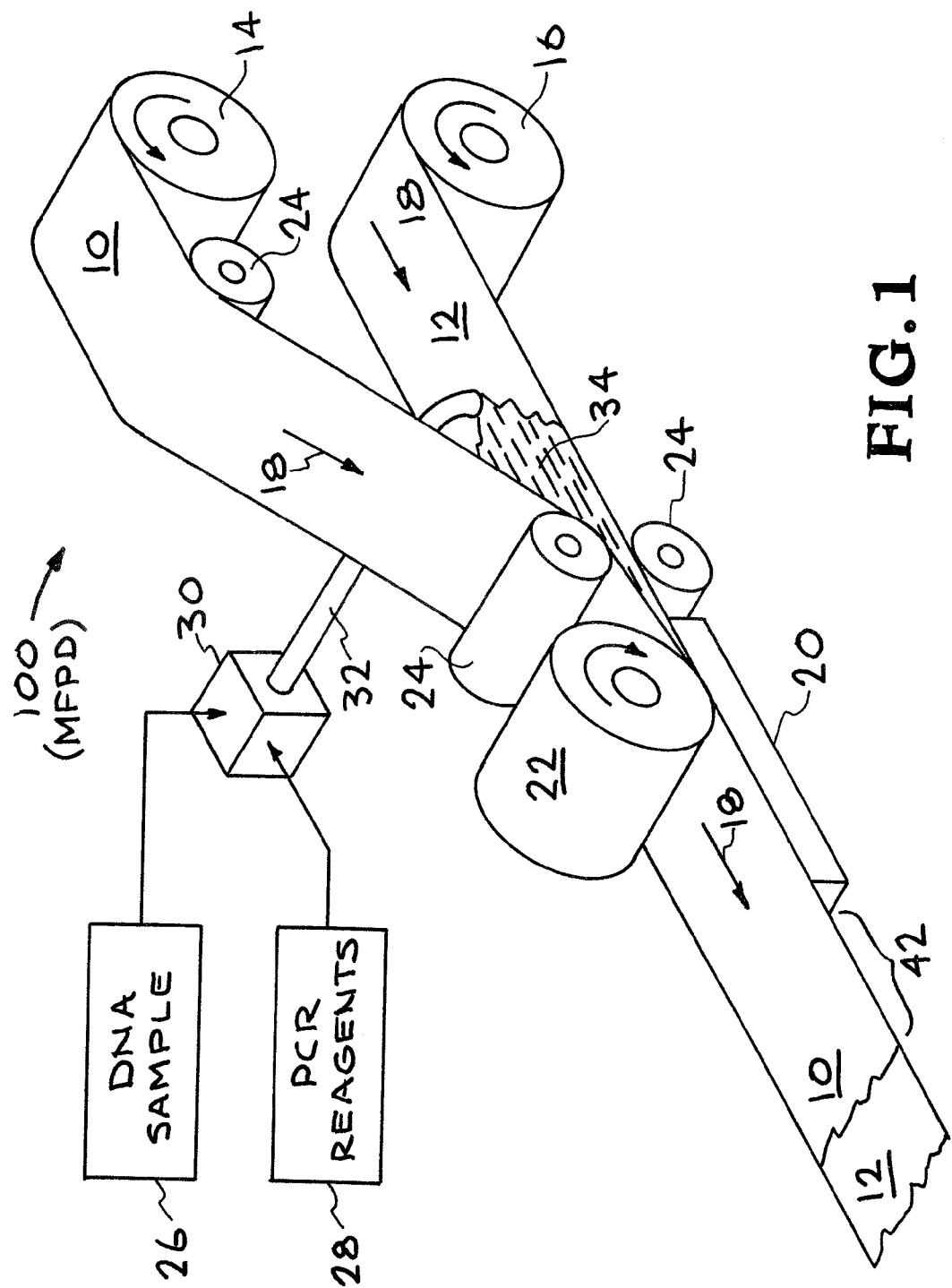
FIG. 1 illustrates one embodiment of the present invention for the encapsulation of fluid partitions between polymeric layers.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides a method for fluid partitioning between polymeric sheets for purposes of chemical amplification, such as PCR-based DNA (or RNA) detection, or for other chemical processing/separations. In some embodiments of the present invention these partitioned fluid "packets" generally have volumes between one micro-liter and one pico-liter. In other embodiments of the present invention, such as chemical separations and/or processing, or cell culture, these partitioned fluid "packets" can have volumes of micro-liters to milli-liters. The fluid to be partitioned is introduced between two polymeric sheets and the sheets are sealed together, for example by thermal bonding, to form an array of independent fluid volumes that do not have fluid communication. In some embodiments the sheets are sealed together prior to the fluid to be partitioned being introduced between two polymeric sheets. The process can be implemented as a batch process or as a continuous process. One embodiment for this fluid partitioning technique is to use two strips of continuous or semi-continuous polymeric film and seal such fluid aliquots, or fluid partitions, between the film layers using a continuous or semi-continuous process. Such a bi-layer polymeric film with sealed fluid partitions can then be fed through various processing and detection equipment as a continuous tape or sheet. The processing and detection equipment can comprise of heating and cooling stages for PCR processing, and optical detection stages for DNA identification.

Micro-Fluidic Partitioning Using Polymeric Film

Referring now to the drawings and in particular to FIG. 1, one embodiment of the present invention is illustrated providing a method of sealing fluid sample by having a heated roller with a surface, that when rolled over the polymeric films containing the fluid layer isolate the fluid sample due to pressure from the grid and thermally-weld a pattern of the two films layers together thereby forming an array of fluid samples or packets of fluid samples. Another embodiment of partitioning the fluid between the polymeric sheets is to first seal the sheets together longitudinally with a multitude of parallel sealing lines, and then to in turn seals the polymeric sheets together with transverse thermally-welded lines. One embodiment is illustrated in FIG. 1. It is to be noted that when using a "roller" approach for sealing the fluid partitions between the polymeric films as is illustrated in FIG. 1, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s).

The embodiment of the present invention illustrate by FIG. 1, depicts apparatus and helps illustrate a method of sealing fluid samples by having a heated roller with a surface, that when rolled over the polymeric films containing the fluid layer isolate the fluid sample due to pressure from the grid and thermally-weld a pattern of the two films layers together thereby forming an array of fluid samples or packets of samples. Additionally, when using a "roller" approach for sealing the fluid partitions between the polymeric films as is illustrated in FIG. 1, it may be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s).

Referring again to FIG. 1, an apparatus for micro-fluidic partitioning between polymeric sheets (MPBPS) is generally indicated at 100 and is made up of the following items. A supply of the upper polymeric sheet 10 is stored on the roll 14. A supply of the lower polymeric sheet 12 is stored on the roll 16. The arrows 18 indicate the direction the two polymeric sheets will move as they are drawn forward. There are two guide rollers 24 that help to position the polymeric sheets. A supply of the DNA sample 26 and a supply of PCR reagents 28 as examples are mixed together in chamber 30 and then deposited as fluid 34 on the lower polymeric sheet 12 by delivery system 32, as the two polymeric sheets 10 and 12 continue to move in the direction of arrow 18 they pass beneath roller 22 which is supported by structure 44 and form the bi-layer structure 42. No specific micro fluidic chambers or "packets" are show in this figure.

FIG. 1 illustrates basic items that are incorporated in a micro-fluidic partitioning between polymeric sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one micro-liter and one pico-liter. For chemical separations and/or processing, or cell cultures, these partitioned fluid "packets" can have volumes of micro-liters to milli-liters. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that are quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example microcasting of one or both of the polymer films on a mold to develop isolated reaction sites. Such casting using silicone rubber has been successful in developing reproducible features with dimensions on the order of 50 μm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 μm were obtained. Microwave welding of a conductive polymer (e.g., polyaniline, polyacetylene, polypyrrole) has been demonstrated, where micro-fluidic channels with widths of 200 μm and 400 μm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning—Chambers in Polymeric Film

Figure 2:
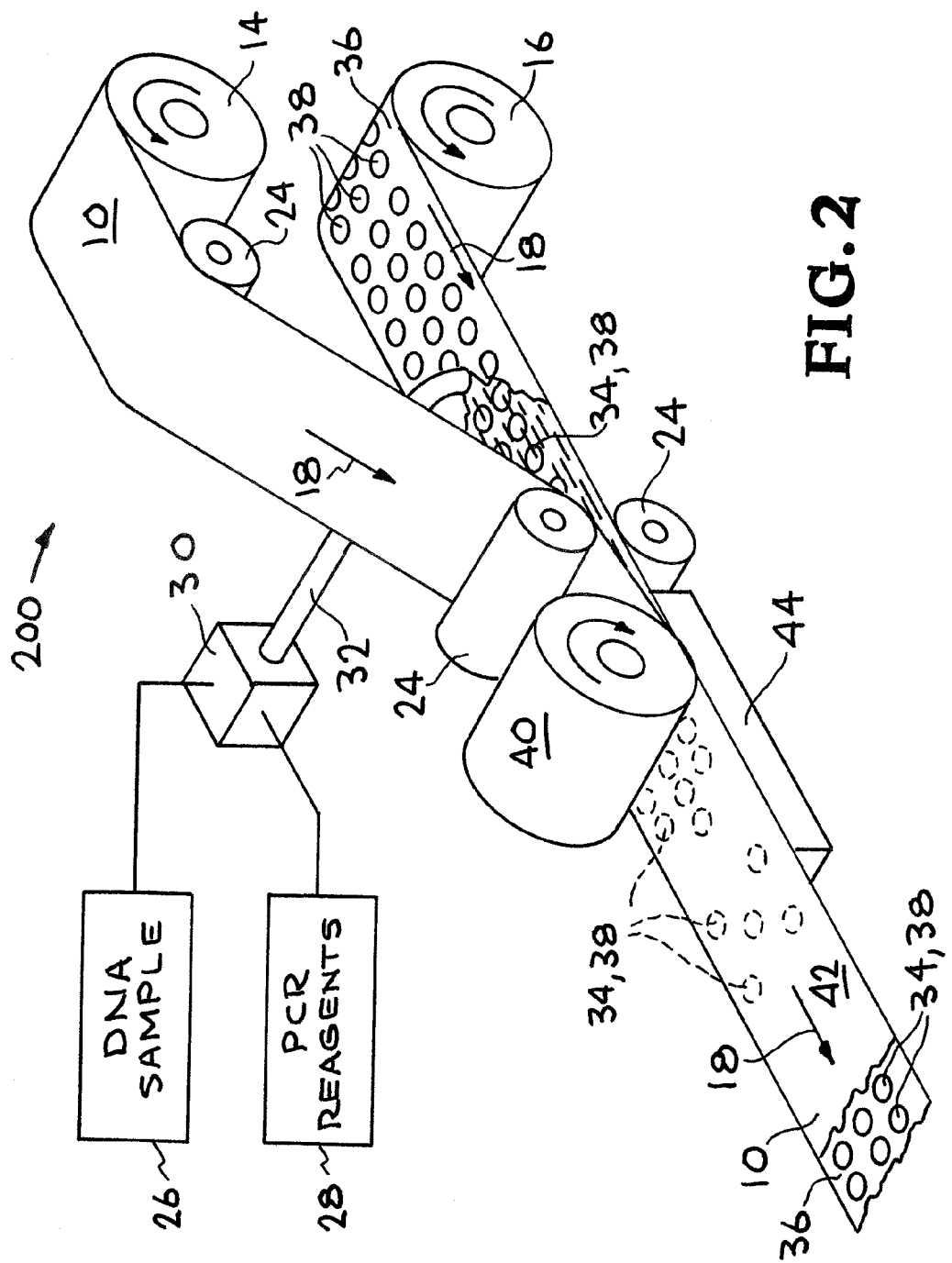
FIG. 2 illustrates another embodiment of the present invention for the encapsulation of fluid partitions between polymeric layers wherein micro-fluid chambers or dimples have been pre-patterned into the lower polymeric sheet.
Figure 3:
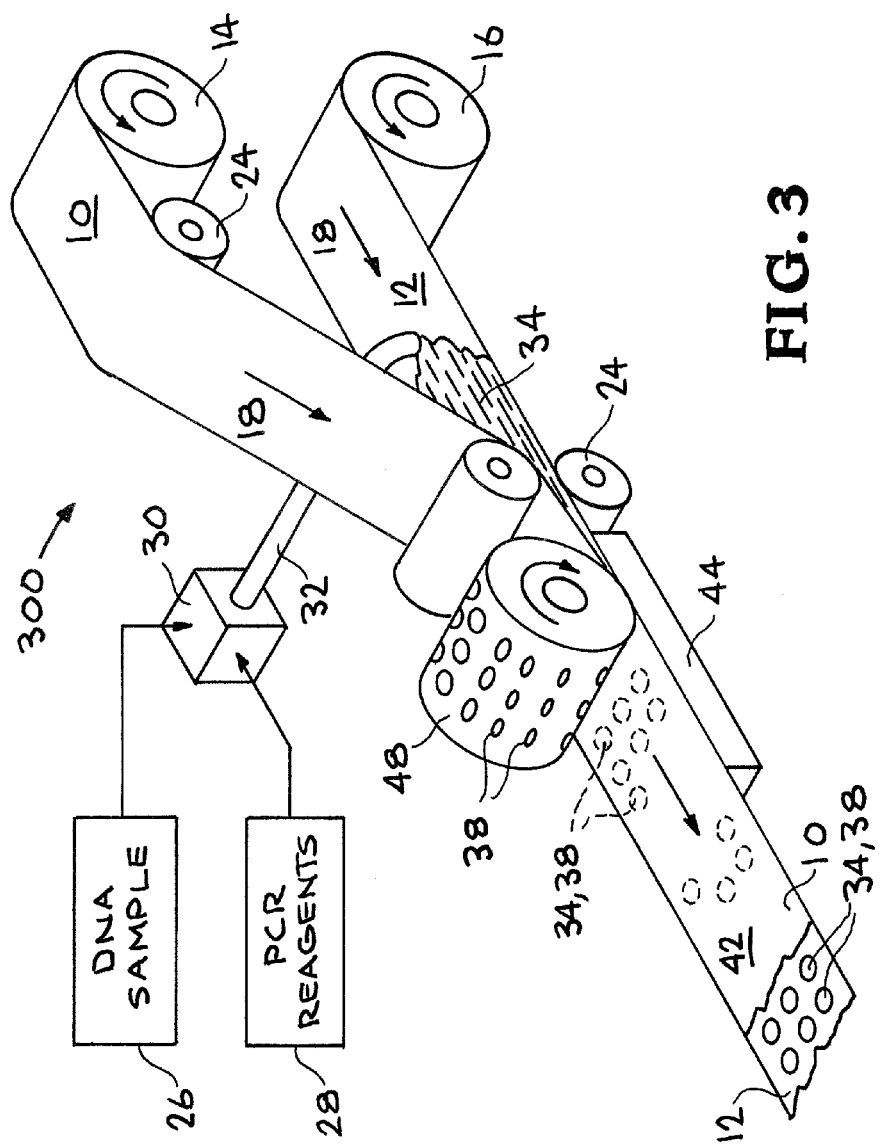
FIG. 3 illustrates another embodiment of the present invention for the encapsulation of fluid partitions between polymeric layers wherein a roller having a patterned template produces circular, oval or square fluid partitions or packets on the polymeric sheet.

Referring now to FIG. 2, another embodiment of the present invention is illustrated providing a method of sealing fluid partitions by having a roller that when rolled over a pair of polymeric films isolates the sample in partitions due to pressure and thermally-welding a grid pattern of the two films layers together thereby forming an array of circular or square fluid partitions or packets. It is to be noted that when using a "roller" approach for sealing the fluid partitions between the polymeric films as is illustrated in FIG. 2, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 2 illustrates a MPBPS apparatus with a pre-patterned polymeric sheet. The MPBPS apparatus is generally indicated at 200 and a number of items that are similar to items shown on FIG. 1 will use the same reference numbers.

In this FIG. 2 the lower polymeric sheet is now designated by the numeral 36 and as can be seen the sheet now has micro-fluid chambers or dimples 38 that have been pre-patterned into polymeric sheet 36. As the polymeric sheets move as shown by the arrows 18 and the fluid sample 34 is deposited onto the lower sheet 36 the fluid 34 will fill the dimples 38 and as the sheets pass beneath the roller 40 which can be called the sealing roller the discrete "packets" are formed. The sealing can be done for example by thermal bonding as previously stated. The present invention provides a system for fluid partitioning for chemical amplification or other chemical processing or separations of a sample, comprising a first dispenser of a first polymeric sheet, wherein the first polymeric sheet contains chambers; a second dispenser of a second polymeric sheet wherein the first dispenser and the second dispenser are positioned so that the first polymeric sheet and the second polymeric sheet become parallel; a dispenser of the fluid positioned to dispense the fluid between the first polymeric sheet and the second polymeric sheet; and a seal unit that seals the first polymeric sheet and the second polymeric sheet together thereby sealing the sample between the first polymeric sheet and the second polymeric sheet and partitioning the fluid for chemical amplification or other chemical processing or separations.

FIG. 2 illustrates basic items that are incorporated in a Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one micro-liter and one pico-liter. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that are quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example microcasting of one or both of the polymer films on a mold to develop isolated reaction sites. Such casting using silicone rubber has been successful in developing reproducible features with dimensions on the order of 50 μm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infra-red welding, laser welding, and ultrasonic welding. Micro ultrasonic welding of polymers has been demonstrated for development and assembly of fluidic components and systems, where weld seam widths between 700-1000 μm were obtained. Microwave welding of a conductive polymer (e.g., polyaniline, polyacetylene, polypyrrole) has been demonstrated, where micro-fluidic channels with widths of 200 μm and 400 μm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning—Rollers with Projections

Figure 4:
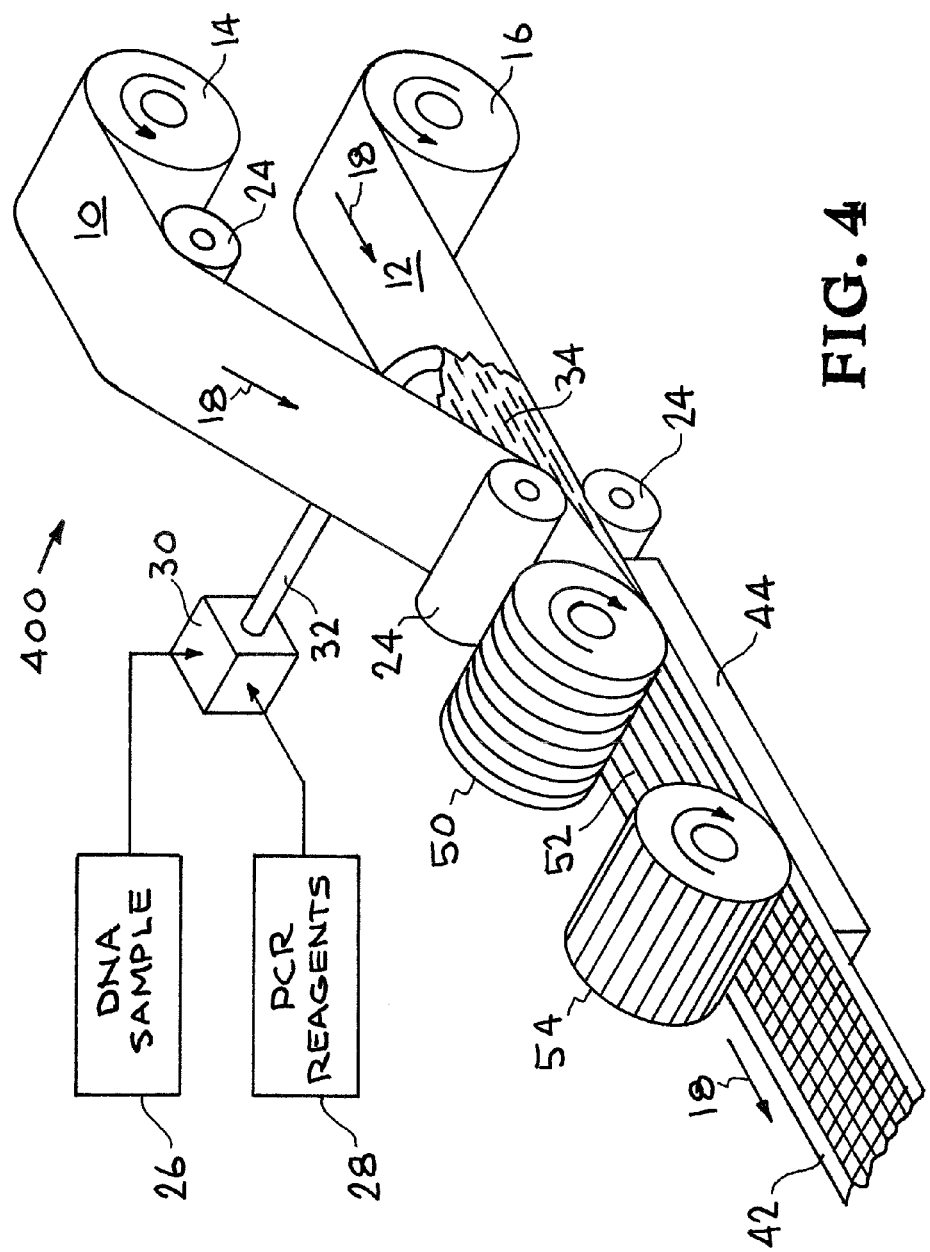
FIG. 4 illustrates another embodiment of the present invention is illustrated providing a method of sealing fluid partitions by having heated rollers with projections that produce a grid surface.

Referring now to FIG. 4, another embodiment of the present invention is illustrated providing a method of sealing fluid partitions by having heated rollers with projections that produce a grid surface. When the rollers are rolled over the polymeric films containing the fluid layer they isolate the fluid partitions due to pressure from the grid and thermally-weld a grid pattern of the two films layers together thereby forming an array of square or other shaped fluid partitions or packets. It is to be noted that when using the "rollers" approach for sealing the fluid partitions between the polymeric films as is illustrated in FIG. 4, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 4 illustrates a MPBPS apparatus with two patterning rollers having a patterned template that produces square fluid partitions or packets on the polymeric sheet. The MPBPS apparatus is generally indicated at 400 and a number of items that are similar to items shown on FIG. 1 will use the same reference numbers.

In FIG. 4 we show a MPBPS apparatus that uses two patterning rollers to form micro-fluidic chambers that are essentially square in shape. (Other embodiments provide different shaped micro-fluidic units) The MPBPS is generally indicated at 400. As can be seen the two polymeric sheets 10 and 12 with sample fluid 34 deposited on the lower sheet 12 now pass beneath a first roller 50 that forms longitudinal patterns 52 in the polymeric sheets and thence to a second roller 54 that forms latitudinal patterns at ninety degrees to the previous pattern 52 thereby forming the square chambers 38. As the polymeric sheets move as shown by the arrows 18 the first roller 50 forms longitudinal patterns 52 in the polymeric sheets and the second roller 54 forms latitudinal patterns at ninety degrees to the previous pattern 52. The fluid sample 34 segregated in the square chambers 38 in the sheet 12 and the sheet 10 and the fluid 34 forms discrete "packets." The present invention provides a system for fluid partitioning for chemical amplification or other chemical processing or separations of a sample, comprising a first dispenser of a first polymeric sheet; a second dispenser of a second polymeric sheet wherein the first dispenser and the second dispenser are positioned so that the first polymeric sheet and the second polymeric sheet become parallel; a dispenser of the sample positioned to dispense the sample between the first polymeric sheet and the second polymeric sheet; and a seal unit that seals the first polymeric sheet and the second polymeric sheet together thereby sealing the sample between the first polymeric sheet and the second polymeric sheet and partitioning the sample for chemical amplification or other chemical processing or separation wherein seal unit that seals the first polymeric sheet and the second polymeric sheet together comprises a first roller with longitudinal projections and a second roller with transverse projections.

FIG. 4 illustrates basic items that are incorporated in a Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one micro-liter and one pico-liter. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that are quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example micro-casting of one or both of the polymer films on a mold to develop isolated reaction sites. Such casting using silicone rubber has been successful in developing reproducible features with dimensions on the order of 50 µm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 µm were obtained. Microwave welding of a conductive polymer (e.g., polyaniline, polyacetylene, polypyrrole) has been demonstrated, where micro-fluidic channels with widths of 200 µm and 400 µm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning—Roller with Projections

Figure 5:
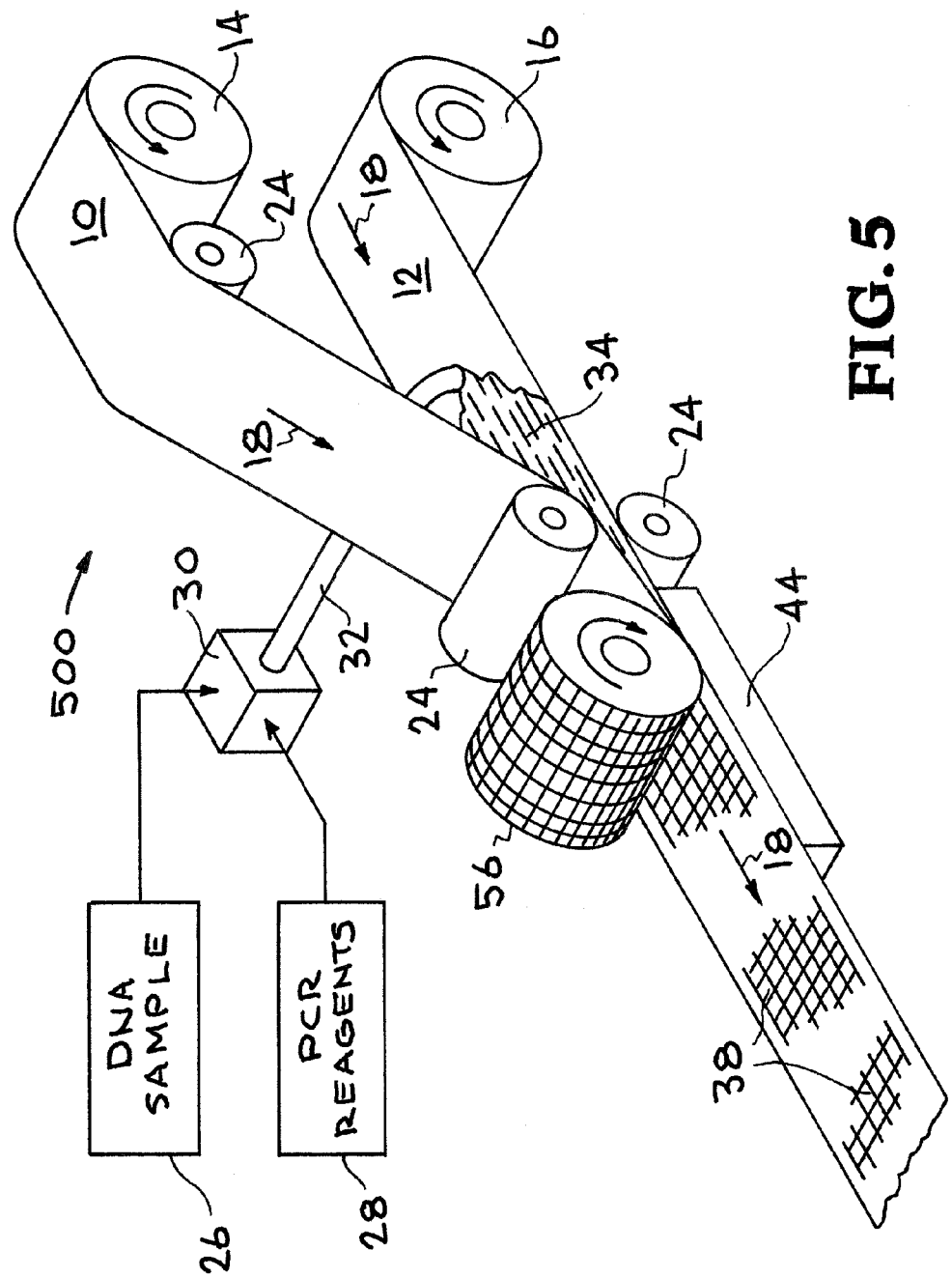
FIG. 5 illustrates another embodiment of the present invention is illustrated providing a method of sealing fluid partitions by having a heated roller with grid projections that produce a grid surface.

Referring now to FIG. 5, another embodiment of the present invention is illustrated providing a method of sealing fluid partitions by having a heated roller with grid projections that produce a grid surface. When the roller is rolled over the polymeric films containing the fluid layer they isolate the fluid partitions due to pressure from the grid and thermally-weld a grid pattern of the two films layers together thereby forming an array of square fluid partitions or packets. It is to be noted that when using the "roller" approach for sealing the fluid partitions between the polymeric films as is illustrated in FIG. 5, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 5 illustrates a MPBPS apparatus with two patterning rollers having a patterned template that produces square fluid partitions or packets on the polymeric sheet. The MPBPS apparatus is generally indicated at 400 and a number of items that are similar to items shown on FIG. 1 will use the same reference numbers.

In FIG. 5 we show a MPBPS apparatus that uses a patterning roller to form micro-fluidic chambers that are essentially square in shape. (Other embodiments provide different shaped micro-fluidic units) The MPBPS is generally indicated at 500. As can be seen the two polymeric sheets 10 and 12 with sample fluid 34 deposited on the lower sheet 12 now pass beneath roller 56 that forms square chambers 38. As the polymeric sheets move as shown by the arrows 18 the roller 56 forms patterns in the polymeric sheets. The fluid sample 34 segregated in the square chambers 38 in the sheet 12 and the sheet 10 and the fluid 34 forms discrete "packets." The apparatus forms essentially square micro-fluidic chambers using a single patterned roller to form the chambers 38. In the MPBPS apparatus the two patterning rollers of FIG. 4 used to form the chambers 38 have been replaced by a single roller 56 which will form the micro-fluidic cambers 38, the roller 56 again can perform as the task of sealing the individual chambers 38. The present invention provides a system for fluid partitioning for chemical amplification or other chemical processing or separations of a sample, comprising a first dispenser of a first polymeric sheet; a second dispenser of a second polymeric sheet wherein the first dispenser and the second dispenser are positioned so that the first polymeric sheet and the second polymeric sheet become parallel; a dispenser of the sample positioned to dispense the sample between the first polymeric sheet and the second polymeric sheet; and a seal unit that seals the first polymeric sheet and the second polymeric sheet together thereby sealing the sample between the first polymeric sheet and the second polymeric sheet and partitioning the sample for chemical amplification or other chemical processing or separation wherein seal unit that seals the first polymeric sheet and the second polymeric sheet together comprises a roller with grid projections.

FIG. 5 illustrates basic items that are incorporated in an apparatus Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one microliter and one pico-liter. For chemical separations and/or processing, or cell cultures, these partitioned fluid "packets" can have volumes of micro-liters to milli-liters. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that are quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example micro-casting of one or both of the polymer films on a mold to develop isolated reaction sites. Such casting using silicone rubber has been successful in developing reproducible features with dimensions on the order of 50 µm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 µm were obtained. Microwave welding of a conductive polymer (e.g., polyaniline, polyacetylene, polypyrrole) has been demonstrated, where micro-fluidic channels with widths of 200 µm and 400 µm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning—Projections

Figure 6:
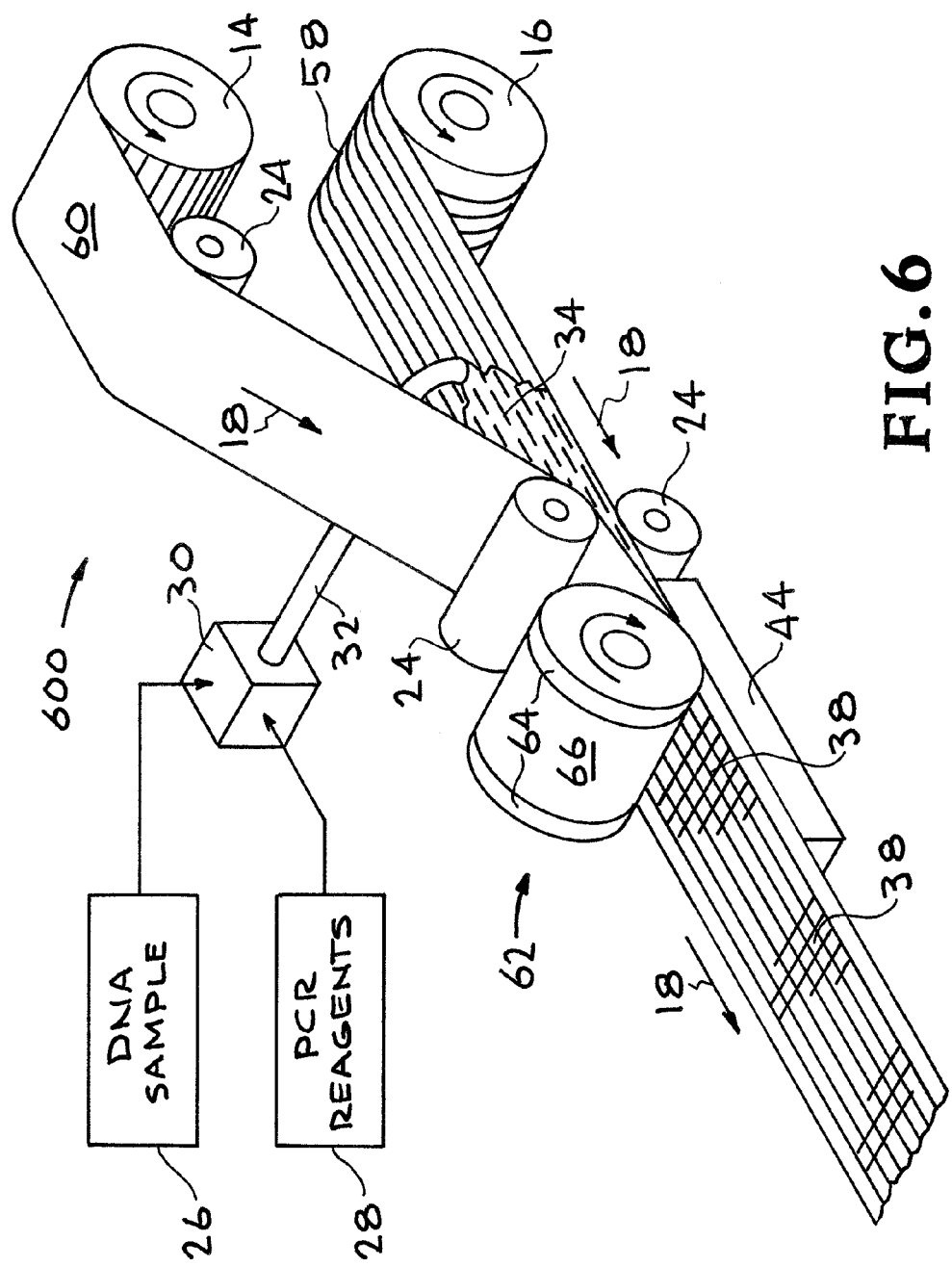
FIG. 6 illustrates an MPBPS apparatus that uses pre-patterned polymeric sheets to form the micro-fluidic chambers.

Referring now to FIG. 6, another embodiment of the present invention is illustrated providing a method of sealing fluid partitions by having a rollers with projection that produce a grid surface when rolled over the polymeric films to isolate the fluid partitions due to pressure from the grid and thermally-weld a grid pattern of the two films layers together thereby forming an array of square fluid partitions or packets. It is to be noted that when using a "roller" approach for sealing the fluid partitions between the polymeric films as is illustrated in FIG. 6, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 6 illustrates a MPBPS apparatus that produces square fluid partitions or packets on the polymeric sheet. The MPBPS apparatus is generally indicated at 600 and a number of items that are similar to items shown on FIG. 1 will use the same reference numbers.

FIG. 6 illustrates an MPBPS apparatus that uses pre-patterned polymeric sheets to form the micro-fluidic chambers 38. The MPBPS apparatus is generally indicated at 600.

In this embodiment of the invention the lower polymeric sheet 58 has been pre-patterned with longitudinal chambers and the upper polymeric sheet has been pre-patterned with latitudinal chambers and as the sheets and sample fluid 34 move under roller 62 the individual chambers 38 are formed. The roller 62 also performs the sealing function. The roller 62 can incorporate areas 64 the will seal the edges of the two polymeric sheets and can also have an area 66 that is compliant or resilient to prevent squashing the micro-fluidic cambers 38. Conversely the support structure 44 could be a resilient or compliant material to perform that function. The present invention provides a system for fluid partitioning for chemical amplification or other chemical processing or separations of a sample, comprising a first dispenser of a first polymeric sheet, wherein the first polymeric sheet contains pre-formed longitudinal projections; a second dispenser of a second polymeric sheet wherein the first dispenser and the second dispenser are positioned so that the first polymeric sheet and the second polymeric sheet become parallel; a dispenser of the sample positioned to dispense the sample between the first polymeric sheet and the second polymeric sheet; and a sealing unit that seals the first polymeric sheet and the second polymeric sheet together thereby sealing the sample between the first polymeric sheet and the second polymeric sheet and partitioning the sample for chemical amplification or other chemical processing or separations, wherein the seal unit that seals the first polymeric sheet and the second polymeric sheet together comprises a roller with transverse projections.

In FIG. 6 we show a MPBPS apparatus that forms micro-fluidic chambers that are essentially square in shape. (Other embodiments provide different shaped micro-fluidic units) As can be seen the two polymeric sheets 58 and 60 with sample fluid 34 deposited on the lower sheet 58 now pass beneath roller 56 that forms square chambers 38. As the polymeric sheets move as shown by the arrows 18 the two polymeric sheets 58 and 60 and roller 66 form patterns in the polymeric sheets. The fluid sample 34 segregated in the square chambers 38 in the sheet 58 and the sheet 60 and the fluid 34 forms discrete "packets." The apparatus forms essentially square micro-fluidic chambers 38.

FIG. 6 illustrates basic items that are incorporated in an apparatus for Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one micro-liter and one pico-liter. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that are quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example microcasting of one or both of the polymer films on a mold to develop isolated reaction sites. Such casting using silicone rubber has been successful in developing reproducible features with dimensions on the order of 50 µm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 µm were obtained. Microwave welding of a conductive polymer (e.g., polyaniline, polyacetylene, polypyrrole) has been demonstrated, where micro-fluidic channels with widths of 200 µm and 400 µm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning—Projections & Laser

Figure 7:
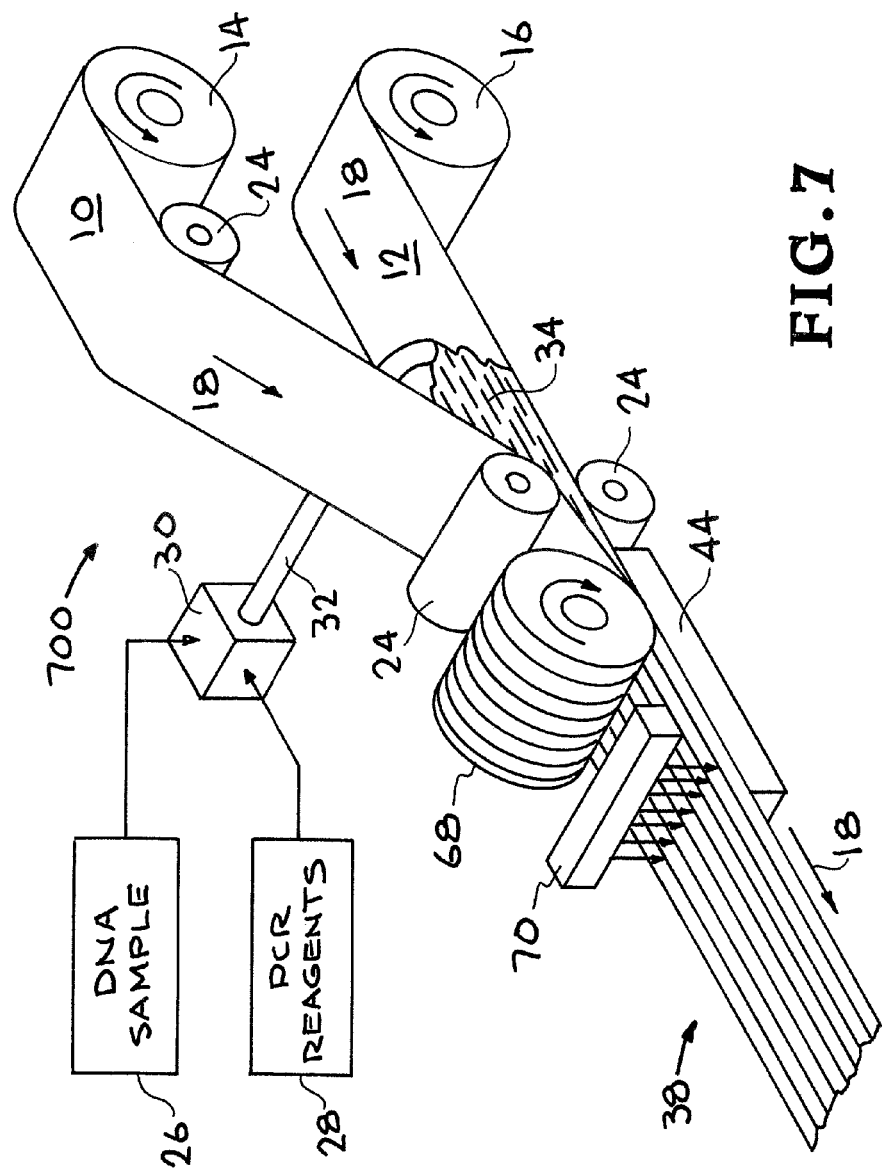
FIG. 7 illustrates another embodiment of the present invention is illustrated providing a method of sealing fluid partitions by having a heated roller with a grid surface, that when rolled over the polymeric films containing the fluid layer isolate the fluid partitions due to pressure from the grid and thermally-weld a grid pattern of the two films layers together thereby forming an array of square fluid partitions or packets.

Referring now to FIG. 7, another embodiment of the present invention is illustrated providing a method of sealing fluid partitions by having a heated roller with a grid surface, that when rolled over the polymeric films containing the fluid layer isolate the fluid partitions due to pressure from the grid and thermally-weld a grid pattern of the two films layers together thereby forming an array of square fluid partitions or packets. It is to be noted that when using a "roller" approach for sealing the fluid partitions between the polymeric films as is illustrated in FIG. 7, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 7 illustrates a MPBPS apparatus that produces square fluid partitions or packets on the polymeric sheet. The MPBPS apparatus is generally indicated at 700 and a number of items that are similar to items shown on FIG. 1 will use the same reference numbers.

FIG. 7 will illustrate one method that can be used to encapsulate the micro-fluidic chambers. Many methods could be used to bond the polymeric films together (i. e., polymer weld) to contain fluid partitions, including but not limited to resistively-heated plates, wires or textured surfaces, induction welding, dielectric welding, microwave welding, infra-red welding, laser welding and ultrasonic welding. The MPBPS apparatus shown here is generally indicated at 700. In this illustration we show long narrow micro-fluidic chambers being sealed using a laser bar 70. The present invention provides a system for fluid partitioning for chemical amplification or other chemical processing or separations of a sample, comprising a first dispenser of a first polymeric sheet, wherein the first polymeric sheet contains pre-formed longitudinal projections; a second dispenser of a second polymeric sheet wherein the first dispenser and the second dispenser are positioned so that the first polymeric sheet and the second polymeric sheet become parallel; a dispenser of the sample positioned to dispense the sample between the first polymeric sheet and the second polymeric sheet; and a seal unit that seals the first polymeric sheet and the second polymeric sheet together thereby sealing the sample between the first polymeric sheet and the second polymeric sheet and partitioning the sample for chemical amplification or other chemical processing or separations, wherein the seal unit that seals the first polymeric sheet and the second polymeric sheet together comprises a laser bar that creates transverse projections in the first polymeric sheet and the second polymeric sheet.

In FIG. 7 we show a MPBPS apparatus that forms micro-fluidic chambers that are essentially square in shape. (Other embodiments provide different shaped micro-fluidic units) As can be seen the two polymeric sheets 10 and 12 with sample fluid 34 deposited on the lower sheet 12 now pass beneath roller 68. As the polymeric sheets move as shown by the arrows 18 the two polymeric sheets 10 and 12 and roller 68 form longitudinal patterns in the polymeric sheets. The long narrow micro-fluidic chambers are sealed using a laser bar 70. The fluid sample 34 segregated in the square chambers in the sheet 10 and the sheet 12 and the fluid 34 forms discrete "packets." The apparatus forms essentially square micro-fluidic chambers 38.

FIG. 7 illustrates basic items that are incorporated in an apparatus for a Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one microliter and one pico-liter. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that are quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example microcasting of one or both of the polymer films on a mold to develop isolated reaction sites. Such casting using silicone rubber has been successful in developing reproducible features with dimensions on the order of 50 μm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 μm were obtained. Microwave welding of a conductive polymer (e.g., polyaniline, polyacetylene, polypyrrole) has been demonstrated, where micro-fluidic channels with widths of 200 μm and 400 μm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning—Pre-Patterned Rollers

Figure 8:
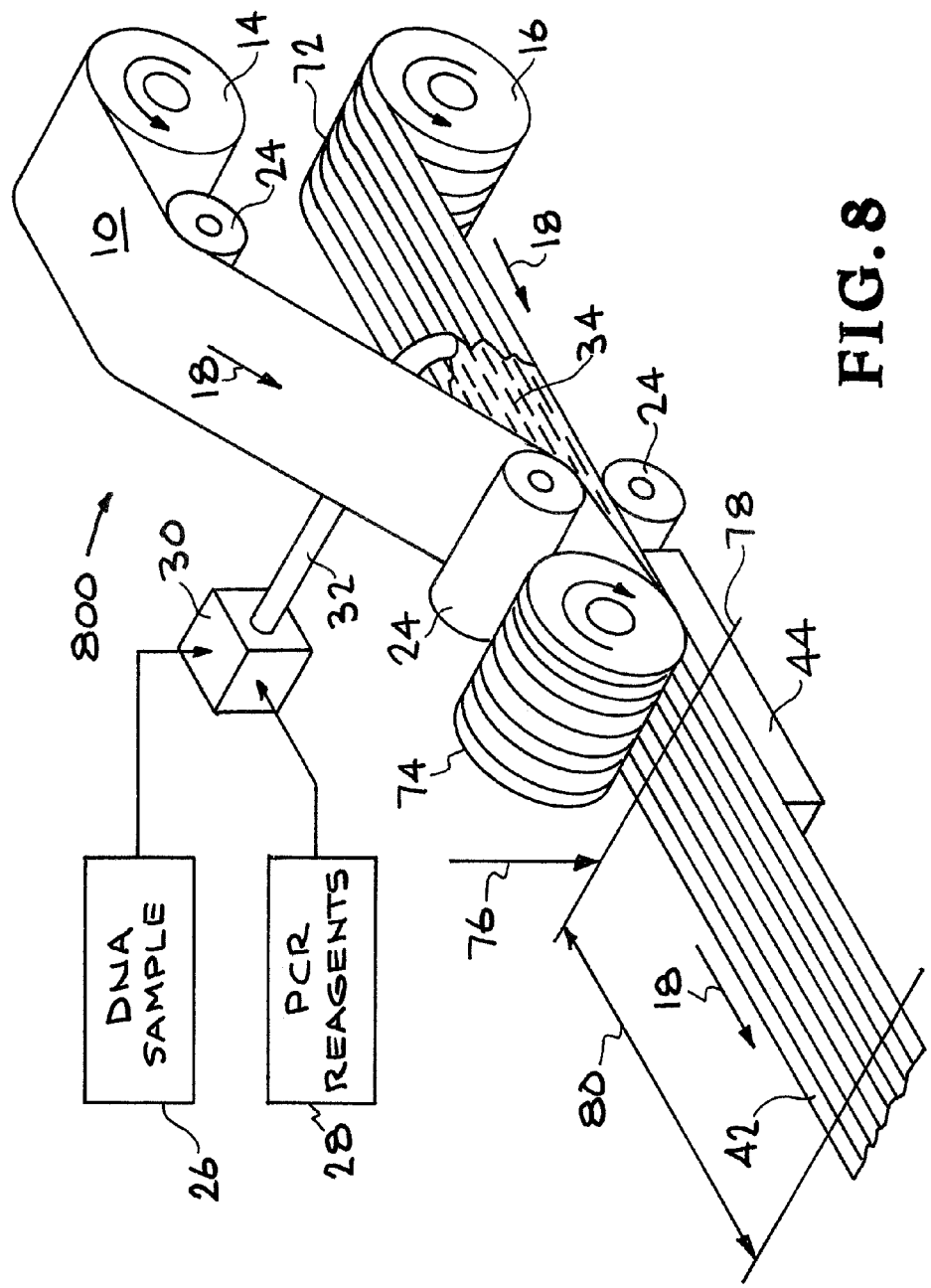
FIG. 8 shows a MPBPS apparatus that forms micro-fluidic chambers that are essentially square in shape.

Referring now to FIG. 8, another embodiment of the present invention is illustrated providing a method of sealing fluid partitions by having heated rollers with projections that produce a grid surface. When the rollers are rolled over the polymeric films containing the fluid layer they isolate the fluid partitions due to pressure from the grid and thermally-weld a grid pattern of the two films layers together thereby forming an array of square fluid partitions or packets. It is to be noted that when using the "rollers" approach for sealing the fluid partitions between the polymeric films as is illustrated in FIG. 8, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 8 illustrates a MPBPS apparatus with two patterning rollers having a patterned template that produces square fluid partitions or packets on the polymeric sheet. The MPBPS apparatus is generally indicated at 400 and a number of items that are similar to items shown on FIG. 1 will use the same reference numbers.

FIG. 8 illustrates an MPBPS apparatus that is generally indicated at 800. In this apparatus a pre-patterned roll of polymeric sheet 72 which feeds along through the apparatus as shown by arrows 18. The lower pre-patterned roll 72 receives the sample fluid 34 and along with upper polymeric sheet 10 pass beneath roller 74. The roller 74 can function as the sealing means or some other sealing means can be used for example the diode laser bar 70 shown on FIG. 7. The long narrow micro-fluidic chambers 38 formed here can then be additionally processed by a laser beam 76 that travels laterally across the array of the long narrow micro-fluidic chambers along the path 78. By adjusting the length of the sections of the long narrow micro-fluidic chambers a section 80 can be created. This technique could be used to produce long narrow chambers of gas, liquid or solids, including gels, between the polymeric films for other applications, for example electrophoreses. The present invention provides a system for fluid partitioning for chemical amplification or other chemical processing or separations of a sample, comprising a first dispenser of a first polymeric sheet, wherein the first polymeric sheet contains pre-formed longitudinal projections; a second dispenser of a second polymeric sheet wherein the first dispenser and the second dispenser are positioned so that the first polymeric sheet and the second polymeric sheet become parallel; a dispenser of the sample positioned to dispense the sample between the first polymeric sheet and the second polymeric sheet; and a seal unit that seals the first polymeric sheet and the second polymeric sheet together thereby sealing the sample between the first polymeric sheet and the second polymeric sheet and partitioning the sample for chemical amplification or other chemical processing or separations, wherein the seal unit that seals the first polymeric sheet and the second polymeric sheet together comprises a roller with longitudinal projection and a laser that creates transverse projections in the first polymeric sheet and the second polymeric sheet.

In FIG. 8 we show a MPBPS apparatus that forms micro-fluidic chambers that are essentially square in shape. (Other embodiments provide different shaped micro-fluidic units) As can be seen the two polymeric sheets 10 and 72 with sample fluid 34 deposited on the lower sheet 72 now pass beneath roller 74. As the polymeric sheets move as shown by the arrows 18 the two polymeric sheets 10 and 72 and roller 74 form longitudinal patterns in the polymeric sheets. The long narrow micro-fluidic chambers are sealed using a laser bar 70 or laser 76. The fluid sample 34 segregated in the square chambers in the sheet 10 and the sheet 72 and the fluid 34 forms discrete "packets." The apparatus forms essentially square micro-fluidic chambers 38.

FIG. 8 illustrates basic items that are incorporated in an apparatus for Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one microliter and one pico-liter. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that are quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example micro-casting of one or both of the polymer films on a mold to develop isolated reaction sites. Such casting using silicone rubber has been successful in developing reproducible features with dimensions on the order of 50 μpm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 μm were obtained. Microwave welding of a conductive polymer (e.g., polyaniline, polyacetylene, polypyrrole) has been demonstrated, where micro-fluidic channels with widths of 200 μm and 400 μm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning—Reduced Section Roller

Figure 9:
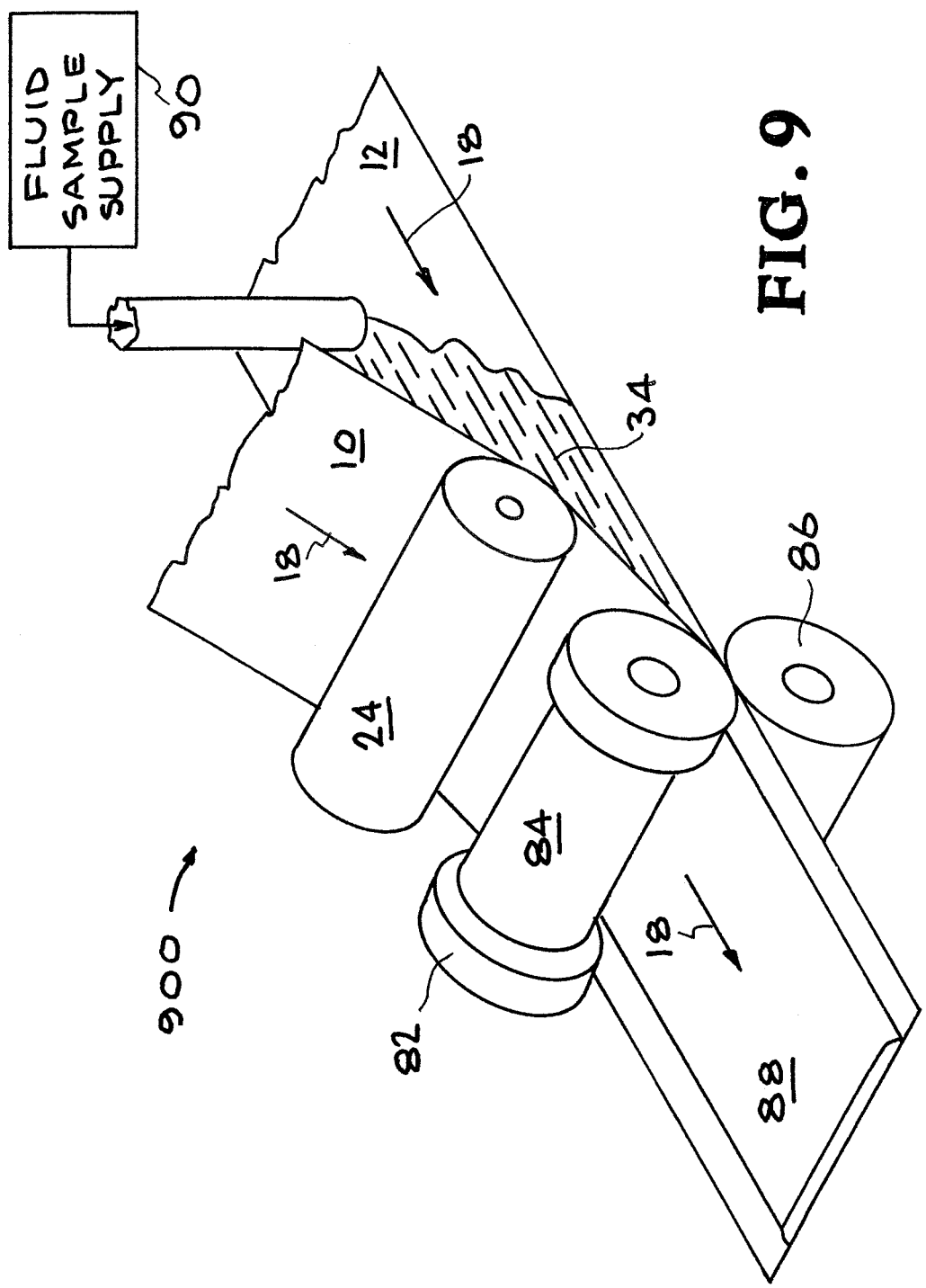
FIG. 9 illustrates an MPBPS apparatus 900 with a method for sealing the edges of the two polymeric sheets.

Referring now to FIG. 9, another embodiment of the present invention is illustrated providing a method of sealing fluid partitions by having a heated roller that when rolled over the polymeric films containing the fluid layer isolate the fluid partitions due to pressure from the grid and thermally-weld a grid of the two films layers together thereby forming fluid partitions or packets. It is to be noted that when using a "roller" approach for sealing the fluid partitions between the polymeric films as is illustrated in FIG. 9, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 9 illustrates a MPBPS apparatus that produces fluid partitions or packets on the polymeric sheet. The MPBPS apparatus is generally indicated at 800 and a number of items that are similar to items shown on FIG. 1 will use the same reference numbers.

FIG. 9 illustrates an MPBPS apparatus 900 with a method for sealing the edges of the two polymeric sheets. The upper polymeric sheet 10 and lower polymeric sheet 12 along with sample fluid 34 from sample fluid supply 90 pass though the roller 82 that is supported by roller 86. As can be seen here the roller 82 has a reduced area 84. The outer sections of the roller 82 will seal the edges of the two polymeric sheets 10 and 12 and the reduced area 84 will allow a sample fluid 34 filled pocket 88 to be created. This fluid filled pocket 88 can be then be further processed to form the desired micro-fluidic chambers.

In FIG. 9 we show a MPBPS apparatus that forms micro-fluidic chambers that are essentially square in shape. (Other embodiments provide different shaped micro-fluidic units) As can be seen the two polymeric sheets 10 and 12 with sample fluid 34 deposited on the lower sheet 72 now pass beneath roller 74. As the polymeric sheets move as shown by the arrows 18 the two polymeric sheets 10 and 12 and roller 86 form longitudinal area in the polymeric sheets. The fluid sample 34 segregated in the longitudinal area in the sheet 10 and the sheet 12 and the fluid 34 forms discrete "packets." The apparatus forms essentially square micro-fluidic chambers 38.

FIG. 9 illustrates basic items that are incorporated in an apparatus for Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one microliter and one pico-liter. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that is quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example micro-casting of one or both of the polymer films on a mold to develop isolated reaction sites. Such casting using silicone rubber has been successful in developing reproducible features with dimensions on the order of 50 µm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 µm were obtained. Microwave welding of a conductive polymer (e.g., polyaniline, polyacetylene, polypyrrole) has been demonstrated, where micro-fluidic channels with widths of 200 µm and 400 µm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning—Roller & Laser

Figure 10:
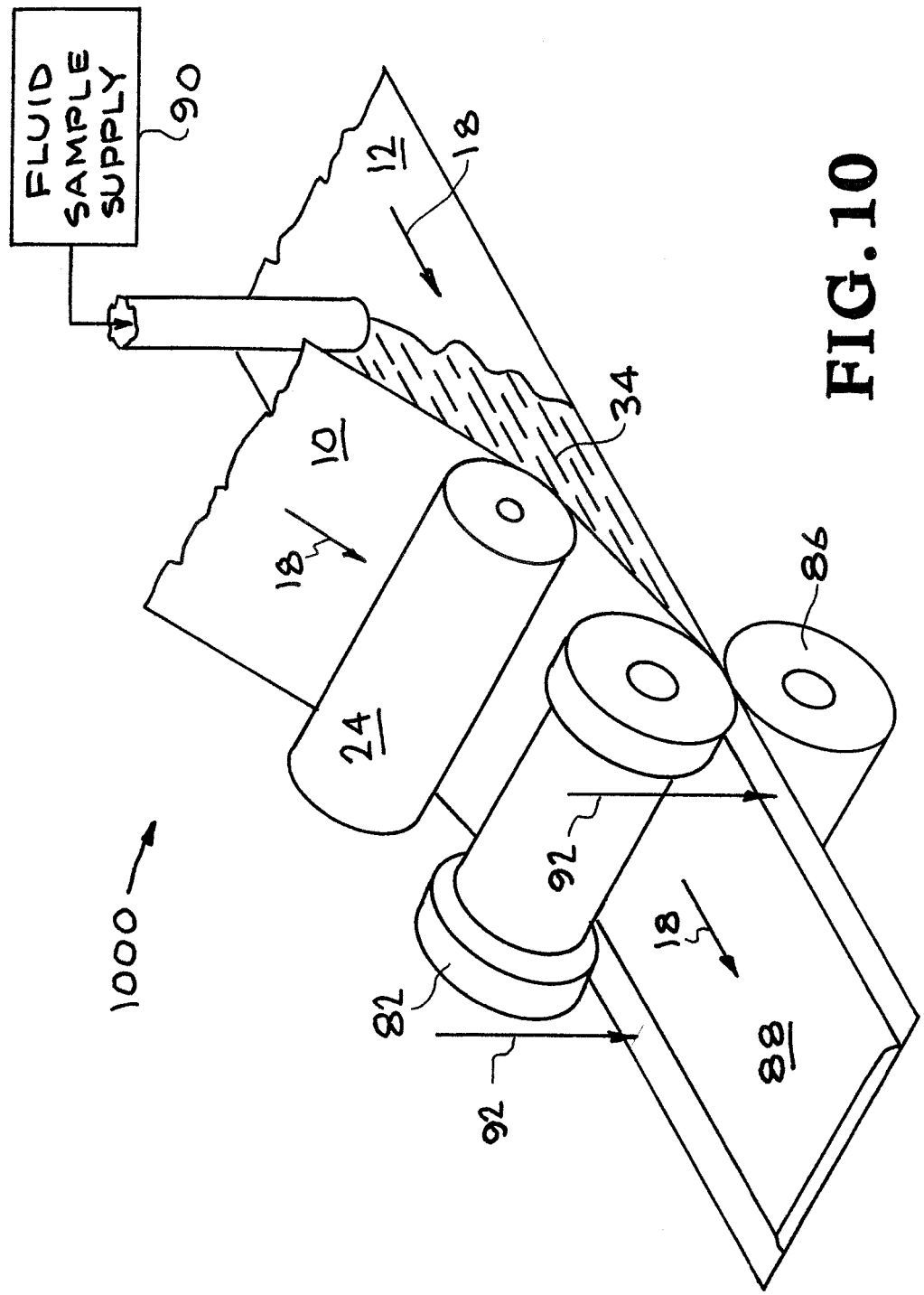
FIG. 10 shows a MPBPS apparatus that forms micro-fluidic chambers that are essentially square in shape.

Referring now to FIG. 10, another embodiment of the present invention is illustrated providing a method of sealing fluid partitions by having a heated roller with a grid surface, that when rolled over the polymeric films containing the fluid layer isolate the fluid partitions due to pressure from the grid and thermally-weld a grid pattern of the two films layers together thereby forming an array of square fluid partitions or packets. It is to be noted that when using a "roller" approach for sealing the fluid partitions between the polymeric films as is illustrated in FIG. 10, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 10 illustrates a MPBPS apparatus that produces square fluid partitions or packets on the polymeric sheet. The MPBPS apparatus is generally indicated at 1000 and a number of items that are similar to items shown on FIG. 1 will use the same reference numbers.

FIG. 10 shows a system 1000 similar to FIG. 6. Here a laser 92 is used to seal the edges of the two polymeric sheets 10 and 12 to form the fluid filled pocket 88.

In FIG. 10 we show a MPBPS apparatus that forms micro-fluidic chambers that are essentially square in shape. (Other embodiments provide different shaped micro-fluidic units) As can be seen the two polymeric sheets 10 and 12 with sample fluid 34 deposited on the lower sheet 12 now pass beneath roller 82. As the polymeric sheets move as shown by the arrows 18 the two polymeric sheets 10 and 12 and roller 82 forms a pattern in the polymeric sheets. The fluid sample 34 segregated in between the sheet 10 and the sheet 12 forms discrete "packets."

FIG. 10 illustrates basic items that are incorporated in an apparatus for Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one microliter and one pico-liter. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that is quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example micro-casting of one or both of the polymer films on a mold to develop isolated reaction sites. Such casting using silicone rubber has been successful in developing reproducible features with dimensions on the order of 50 μm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 μm were obtained. Microwave welding of a conductive polymer (e.g., polyaniline, polyacetylene, polypyrrole) has been demonstrated, where micro-fluidic channels with widths of 200 μm and 400 μm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning Using Light Source

Figure 11:
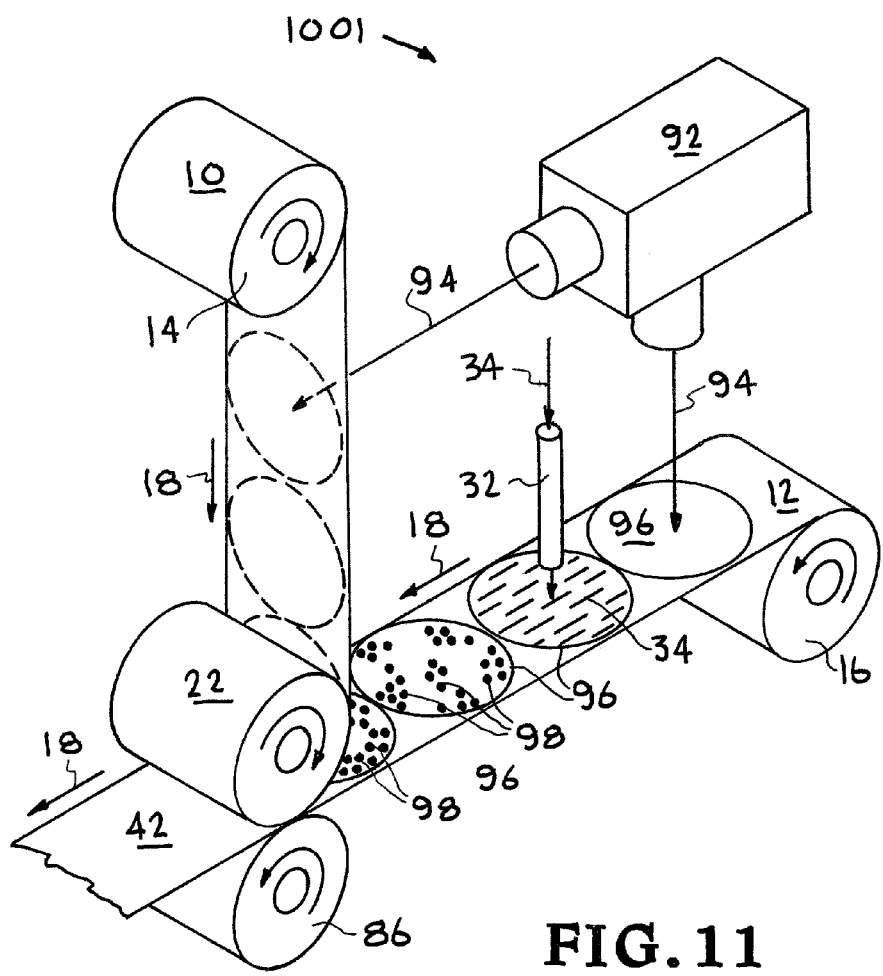
FIG. 11 illustrates another embodiment of the present invention for the encapsulation of fluid partitions between polymeric layers wherein at least one of the films having been conditioned with a light source.

Referring now to FIG. 11, another embodiment of the present invention is illustrated providing a system for fluid partitioning for chemical amplification or other chemical processing or separations of a sample. The fluid partitioning of the sample is accomplished by sealing fluid partitions by having a roller that when rolled over a pair of polymeric films, at least one of the films having been conditioned with a light source, provides an array of independent sample fluid volumes that do not have fluid communication. When the roller is rolled over the pair of polymeric films with at least one of the films having been conditioned with a light source, the polymeric films are sealed together by pressure and a thermal weld thereby forming an array of fluid partitions or packets. It is to be noted that when using a "roller" approach for sealing the fluid partitions between the polymeric films as is illustrated in FIG. 11, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 11 illustrates a MPBPS apparatus that produces square fluid partitions or packets on the polymeric sheet. The MPBPS apparatus is generally indicated at 1001 and a number of items that are similar to items shown on FIG. 1 will use the same reference numbers.

FIG. 11 illustrates a MPBPS apparatus 1001 that uses a light source 92 to alter the surface properties of the polymeric film. In this illustrated apparatus we again have an upper polymeric film 10 a supply of which is stored on roll 14 and a lower polymeric film 12 a supply of which is stored on roll 16. Both the upper film 10 and lower film 12 will move in the direction of arrows 18. The light source 92 that for example can be a laser delivering femtosecond pulses of light, will alter the surface of films 12 to make it hydrophilic.

The altered area is designated as 96. The sample fluid 34 is deposited on the altered area 96 by the delivery system 32. Because the altered surface 96 is now hydrophilic this will cause the sample fluid 34 to form a large number of milli- to pico-liter droplets. The two polymeric films 10 and 12 now are joined together as they pass through sealing roller 22 and support roller 86 and the two films now are formed into a bi-layer structure with 42 with sample 34 milli- to pico-liter droplets sealed between the two layers. The present invention provides a system for fluid partitioning for chemical amplification or other chemical processing or separations of a sample, comprising a first dispenser of a first polymeric sheet; a second dispenser of a second polymeric sheet wherein the first dispenser and the second dispenser are positioned so that the first polymeric sheet and the second polymeric sheet become parallel; a dispenser of the fluid positioned to dispense the fluid between the first polymeric sheet and the second polymeric sheet; a chip for producing a magnetic field on the first polymeric sheet forming the sample into milli- to pico-liter droplets oriented into a grid array; and a seal unit that seals the first polymeric sheet and the second polymeric sheet together thereby sealing the sample between the first polymeric sheet and the second polymeric sheet and partitioning the fluid for chemical amplification or other chemical processing or separations.

In FIG. 11 we show a MPBPS apparatus that forms micro-fluidic chambers. As can be seen the two polymeric sheets 10 and 12 with sample fluid 34 deposited on the lower sheet 12. As the polymeric sheets move as shown by the arrows 18 the two polymeric sheets 10 are sealed. The fluid sample 34 is segregated between the sheet 10 and the sheet 12 and forms discrete "packets." The present invention provides a system for fluid partitioning for chemical amplification or other chemical processing or separations of a sample, comprising a first dispenser of a first polymeric sheet; a second dispenser of a second polymeric sheet wherein the first dispenser and the second dispenser are positioned so that the first polymeric sheet and the second polymeric sheet become parallel; a dispenser of the fluid positioned to dispense the fluid between the first polymeric sheet and the second polymeric sheet; a light source for conditioning the first polymeric sheet to receive the sample; and a seal unit that seals the first polymeric sheet and the second polymeric sheet together thereby sealing the sample between the first polymeric sheet and the second polymeric sheet and partitioning the fluid for chemical amplification or other chemical processing or separations.

FIG. 11 illustrates basic items that are incorporated in an apparatus for Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one micro-liter and one pico-liter. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that is quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example microcasting of one or both of the polymer films on a mold to develop isolated reaction sites. Such casting using silicone rubber has been successful in developing reproducible features with dimensions on the order of 50 µm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 µm were obtained. Microwave welding of a conductive polymer (e.g., polyaniline, polyacetylene, polypyrrole) has been demonstrated, where micro-fluidic channels with widths of 200 µm and 400 µm were achieved. Low-frequency induction heating has been used for sealing micro-fluidic systems. A nineteen-emitter diode laser bar has been employed in the welding of polymer micro-fluidic devices. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Micro-Fluidic Partitioning Using Magnetic Fields

Figure 12:
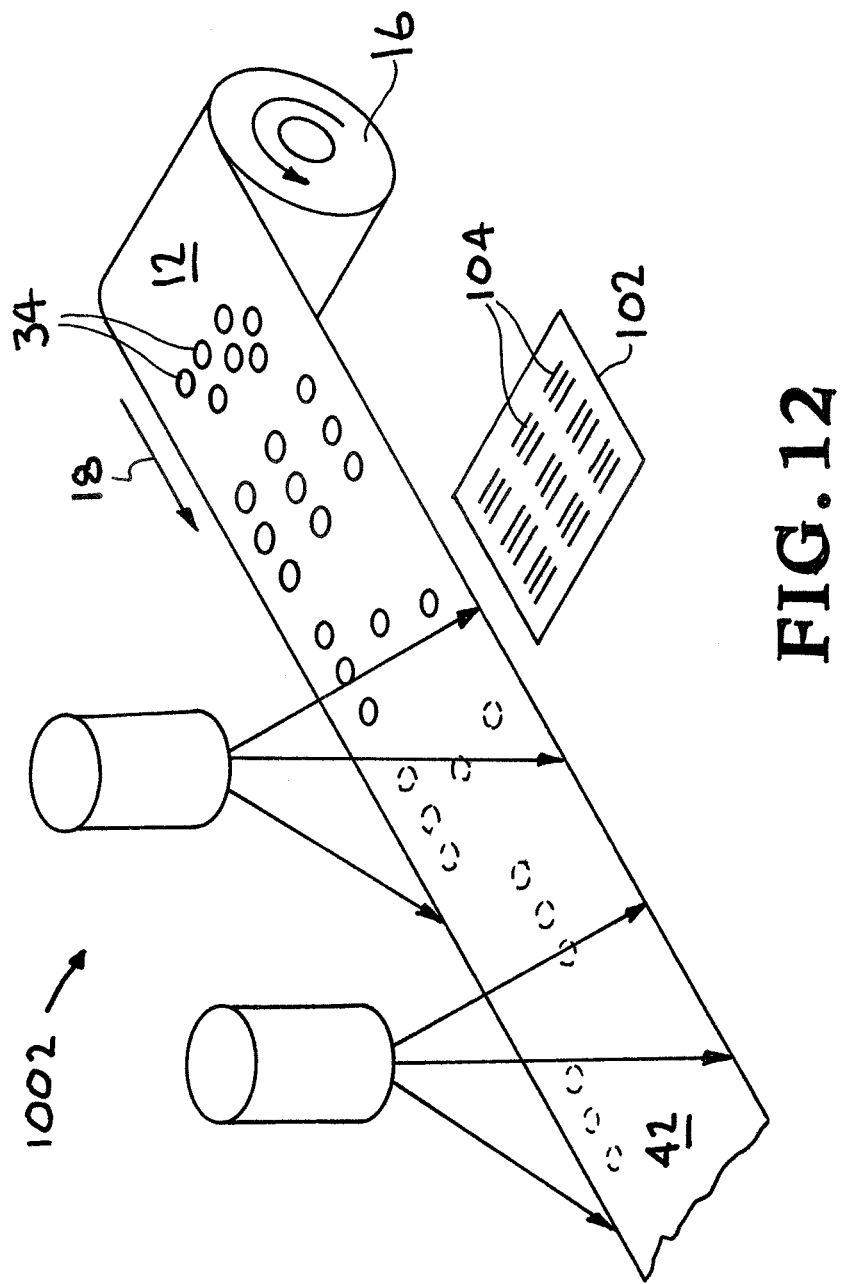
FIG. 12 illustrates another embodiment of the present invention for the encapsulation of a sample using magnetic fields for fluid partitioning.

Referring now to FIG. 12, another embodiment of the present invention is illustrated providing a system for sealing fluid partitions using magnetic fields for fluid partitioning for chemical amplification or other chemical processing or separations of a sample. The fluid partitioning of the sample is accomplished by sealing fluid partitions by having a roller that when rolled over a pair of polymeric films, at least one of the films having milli- to pico-liter-droplets of the sample fluid deposited on the film and the milli- to pico-liter-droplets oriented into a grid array.

When the roller is rolled over the pair of polymeric films with at least one of the films having milli- to pico-liter-droplets of the sample fluid deposited on the film and the milli- to pico-liter-droplets oriented into a grid array, the polymeric films are sealed together by pressure and a thermal weld thereby forming an array of fluid partitions or packets. It is to be noted that when using a "roller" approach for sealing the fluid partitions between the polymeric films as is illustrated in FIG. 12, it can be desirable to first seal the edges of the film during, or immediately before liquid insertion, prior to the remaining longitudinal and horizontal sealing lines (or curves), to retain all test sample between the polymeric sheets. The shape of the lower support surface(s) may need to be modified to increase the time the film is in contact with the sealing roller(s). FIG. 12 illustrates a MPBPS apparatus that produces square fluid partitions or packets on the polymeric sheet. The MPBPS apparatus is generally indicated at 1001 and a number of items that are similar to items shown on FIG. 1 will use the same reference numbers.

FIG. 12 is an MPBPS apparatus that uses magnetic fields to orient milli- to pico-liter-droplets in a grid pattern. A supply of polymeric film 12 is stored on a roll 16. Milli- to pico-liter-droplets of sample fluid 34 have been randomly deposited on the film 12 and as the film moves along as indicated by arrow 18 a section of the film on which the droplets have been deposited passes over a chip 102. The chip 102 has a number of sites fabricated in a grid pattern on the chip and these sites generate magnetic fields. The magnetic fields that have been generated by the chip will orient the randomly deposited milli- to pico-liter-droplets into a grid array. It is to be understood that the milli- to pico-liter-droplets and the sites of the chip are show at greatly increased size for illustrative purposes and that in reality these items would be very small and that a large number of the droplets and sites would be produced in this apparatus. After the milli- to pico-liter-droplets have been arrayed on the film the film continues to move along and now a polymer spray apparatus covers the droplets with a thin coating of polymer and at the next position a ultraviolet source is used to cure the sprayed on polymer coating and now we end up with a product 42 that is again a bi-layer sandwich of a polymer film 12 with milli- to pico-liter-droplets of a sample fluid that have been covered with a layer of polymeric spray that has subsequently been cured and we now have an array of trapped milli- to pico-liter-droplets in a grid pattern ready for analysis. The sprayed on film of polymer can be transparent (as could be the upper film in previous illustrated apparatuses) that facilitate optical analysis of a sample fluid.

In FIG. 12 we show a MPBPS apparatus that forms micro-fluidic chambers. As can be seen the two polymeric sheets 10 and 12 with sample fluid 34 deposited on the lower sheet 12. As the polymeric sheets move as shown by the arrows 18 the two polymeric sheets 10 are sealed. The fluid sample 34 is segregated between the sheet 10 and the sheet 12 and forms discrete "packets." The present invention provides a system for fluid partitioning for chemical amplification or other chemical processing or separations of a sample, comprising a first dispenser of a first polymeric sheet; a second dispenser of a second polymeric sheet wherein the first dispenser and the second dispenser are positioned so that the first polymeric sheet and the second polymeric sheet become parallel; a dispenser of the fluid positioned to dispense the fluid between the first polymeric sheet and the second polymeric sheet; a chip for producing a magnetic field on the first polymeric sheet forming the sample into milli- to pico-liter-droplets oriented into a grid array; and a seal unit that seals the first polymeric sheet and the second polymeric sheet together thereby sealing the sample between the first polymeric sheet and the second polymeric sheet and partitioning the fluid for chemical amplification or other chemical processing or separations.

FIG. 12 illustrates basic items that are incorporated in an apparatus for Micro-fluidic Partitioning Between Polymeric Sheets (MPBPS). The present invention presents a system for fluid portioning between two polymeric sheets for purposes of chemical amplification, such as Polymerase Chain Reaction (PCR)-based DNA (or RNA) detection, or for other chemical processing/separations. These partitioned fluid "packets" generally have volumes between one microliter and one pico-liter. The fluid to be partitioned is introduced between two polymeric sheets and the sheets are sealed together, for example by thermal bonding, to form an array of independent fluid volumes that do not have fluid communication. Such a polymeric bi-layer with sealed independent fluid partitions can then be fed through various processing and detection equipment, for example heating and cooling stages for PCR processing and optical detection stages for DNA detection, enhanced drug discovery, rapid pathogen detection, and rapid multiplexed simultaneous detection of multiple DNA strands.

Many other methods and apparatus for sealing the polymeric films together are included as part of the present invention. For example, other methods and apparatus for sealing the polymeric films together include patterned-sealing with a continuous process and/or using a batch process with polymeric sheets. Such bi-layer polymeric films containing arrays of fluid partitions would be relatively robust, prevent contamination of the fluid aliquots once sealed, and can be processed through heating and cooling cycles, perhaps using heat-conductive films. Additionally, such films can be transparent and easily allow optical interrogation of the samples, with perhaps the lower polymeric layer being reflective to the fluorescent emissions to effectively increase optical path length for detection. The systems described herein for encapsulating fluid partitions between polymeric films would tend to produce fluid volumes that have thicknesses (i.e., the dimension normal to the surface of the polymer films) that is quite smaller than the transverse dimensions. To obtain fluid volumes that are more symmetrical, the polymer films can be pre-treated prior to liquid insertion by developing arrays of wells or dimples in the films where the fluid volumes will be contained. Additionally, other methods may also be used to develop depressions or volumes in the polymeric films, for example microcasting of one or both of the polymer films on a mold to develop isolated reaction sites. Such casting using silicone rubber has been successful in developing reproducible features with dimensions on the order of 50 µm.

Note that similar bonding techniques can be employed to encapsulate long narrow tubes of gas, liquid, or solids, including gels, between the polymeric films for other applications, for example electrophoreses. Many methods can be used to bond the polymeric films together (i.e., polymer weld) to contain fluid partitions, including but not limited to, resistively-heated plates, wires or textured surfaces, induction welding, dielectric welding, microwave welding, infrared welding, laser welding, and ultrasonic welding. Micro ultrasonic welding of polymers has been demonstrated for development and assembly of fluidic components and systems, where weld seam widths between 700-1000 µm were obtained. Microwave welding of a conductive polymer (e.g., polyaniline, polyacetylene, polypyrrole) has been demonstrated, where micro-fluidic channels with widths of 200 µm and 400 µm were achieved. Low-frequency induction heating has been used for sealing micro-fluidic systems. A nineteen-emitter diode laser bar has been employed in the welding of polymer micro-fluidic apparatus. Lasers offer many opportunities and advantages over other polymer welding techniques, including real time bond monitoring, multiple energy sources, and localized bond formation without exterior surface melting. Additionally, other visible light sources, including flash lamps, have been used to weld plastic. Line welds and even patterned welds of plastic can be accomplished with lasers. For laser welding of two polymeric films, one film should be transparent to the laser light and the other film should be relatively absorptive.

Figure 13:
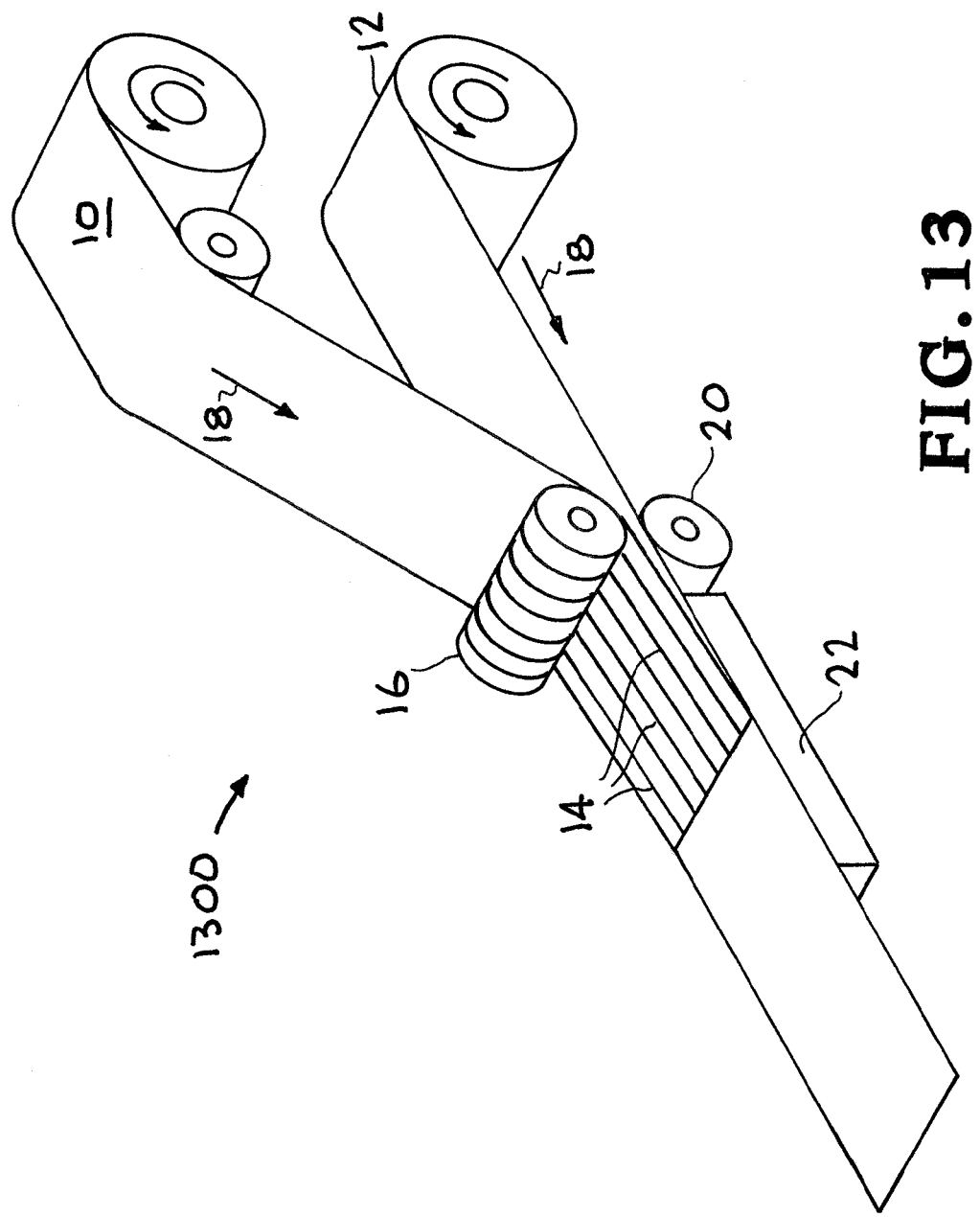
FIG. 13 illustrates another embodiment of the present invention is illustrated providing a method of sealing fluid partitions by providing ridges between the layers.

Referring now to FIG. 13, another embodiment of the present invention is illustrated providing a method of sealing fluid partitions by providing ridges between the layers. In FIG. 13 we show a MFPD device that uses two rolls of polymeric sheets to form micro-fluidic chambers. The MFPD is generally indicated at 1300. As can be seen the two polymeric sheets 10 and 12 are ultimately positioned together. The polymeric sheet 12 on the first roller has longitudinal ridges 14. It is to be understood that the ridges 14 could also be formed in sheet 12 by an additional roller.

The rollers 16 and 20 assist in positioning the polymeric together. The sides of the sheets 10 and 12 can be sealed for sealing the fluid between the polymeric films 10 and 12 as is illustrated in connection with other drawing figures. In some embodiments it can be desirable to first seal the edges of the film during, or immediately before liquid insertion, prior to the remaining longitudinal sealing lines (or parallel capillaries 14), to retain the sample fluid between the polymeric sheets 10 and 12.

A dispenser of the sample is positioned to dispense the sample between the first polymeric sheet and the second polymeric sheet. In some embodiments a seal unit that seals the first polymeric sheet and the second polymeric sheet together sealing the sample between the first polymeric sheet and the second polymeric sheet and an another unit partitions the sample for chemical amplification or other chemical processing or separation wherein the seal units seal the first polymeric sheet and the second polymeric sheet together.

Micro-Fluidic Partitioning—Grid Stamping

Figure 14:
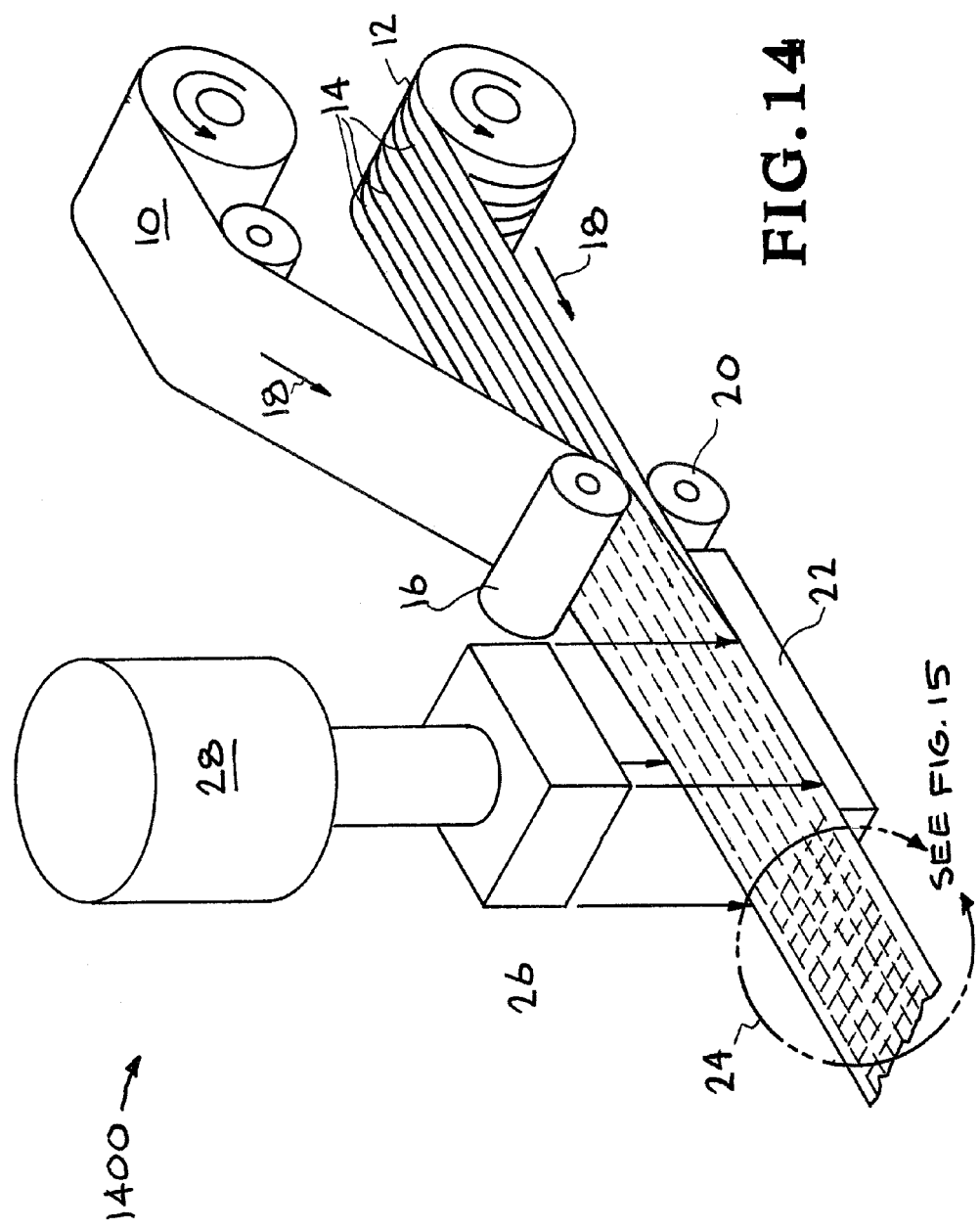
FIG. 14 illustrates another embodiment of the present invention providing a method of sealing fluid partitions using ridges between the layers and creating micro-packets by stamping.
Figure 15:
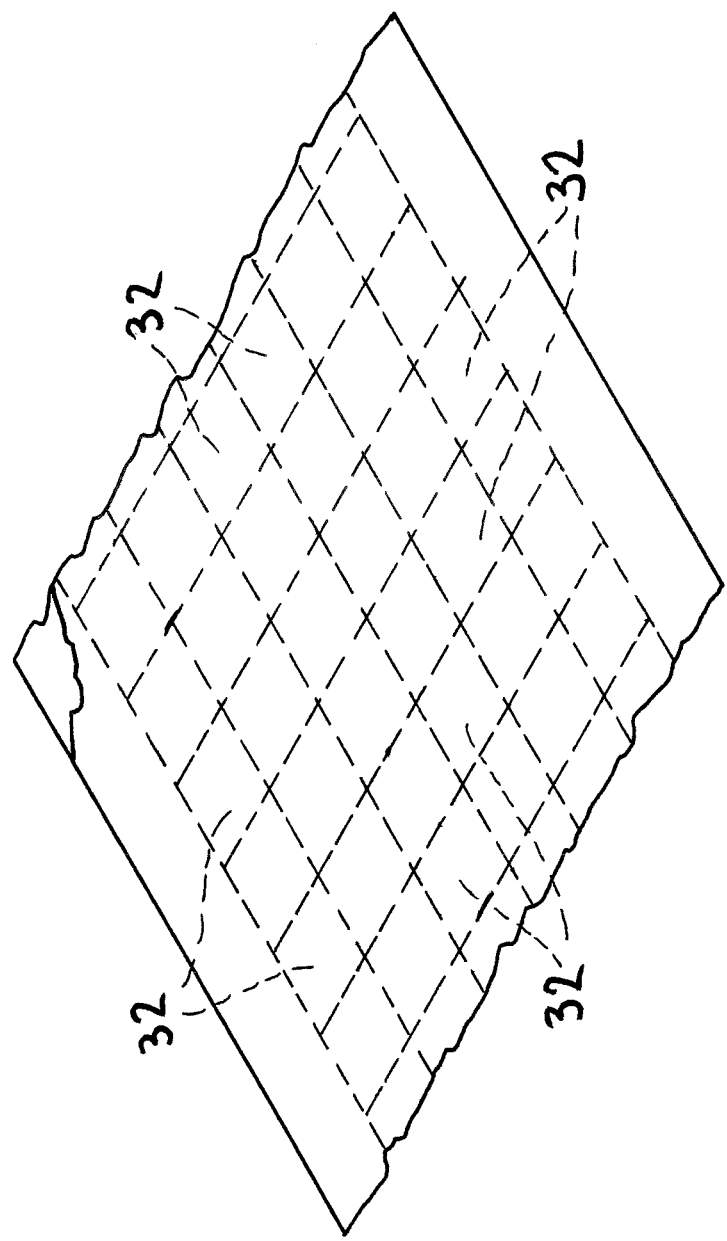
FIG. 15 illustrates another embodiment of the present invention providing a method of sealing fluid partitions using ridges between the layers and creating micro-packets by stamping.

Referring now to FIG. 14 AND FIG. 15, another embodiment of the present invention is illustrated providing a method of sealing fluid partitions using ridges between the layers and creating micro-packets by stamping. In FIG. 14 AND FIG. 15 we show a MPBPS apparatus that uses two rolls of polymeric sheets to form micro-fluidic chambers 32. The MPBPS is generally indicated at 1300. As can be seen the two polymeric sheets 10 and 12 are ultimately positioned together. The polymeric sheet 12 on the first roller has longitudinal ridges 14. It is to be understood that the ridges 14 could also be formed in sheet 12 by an additional roller.

The rollers 16 and 20 assist in positioning the polymeric together. The sides of the sheets 10 and 12 can be sealed for sealing the fluid between the polymeric films 10 and 12 as is illustrated in connection with other drawing figures. In some embodiments it can be desirable to first seal the edges of the film during, or immediately before liquid insertion, prior to the remaining longitudinal sealing lines (or ridges 14), to retain the sample fluid between the polymeric sheets 10 and 12.

A dispenser of the sample is positioned to dispense the sample between the first polymeric sheet and the second polymeric sheet. In some embodiments a seal unit that seals the first polymeric sheet and the second polymeric sheet together thereby sealing the sample between the first polymeric sheet and the second polymeric sheet. A stamping unit 28 uses a stamp 26 with a grid pattern to stamp the sheets 10 and 12 in the area designated by the dotted lines 24 and form partitions 32 of the sample for chemical amplification or other chemical processing or separation.

Micro-Fluidic Partitioning—Batch Processing

Figure 16:
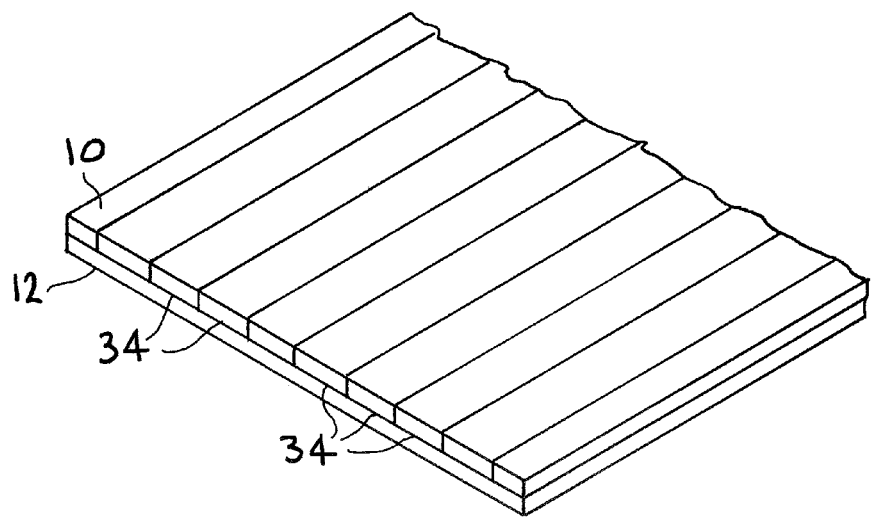
FIG. 16 illustrates an embodiment of the present invention providing a method of sealing fluid partitions using longitudinal cavities between the layers and creating microreactors by batch processing.
Figure 17:
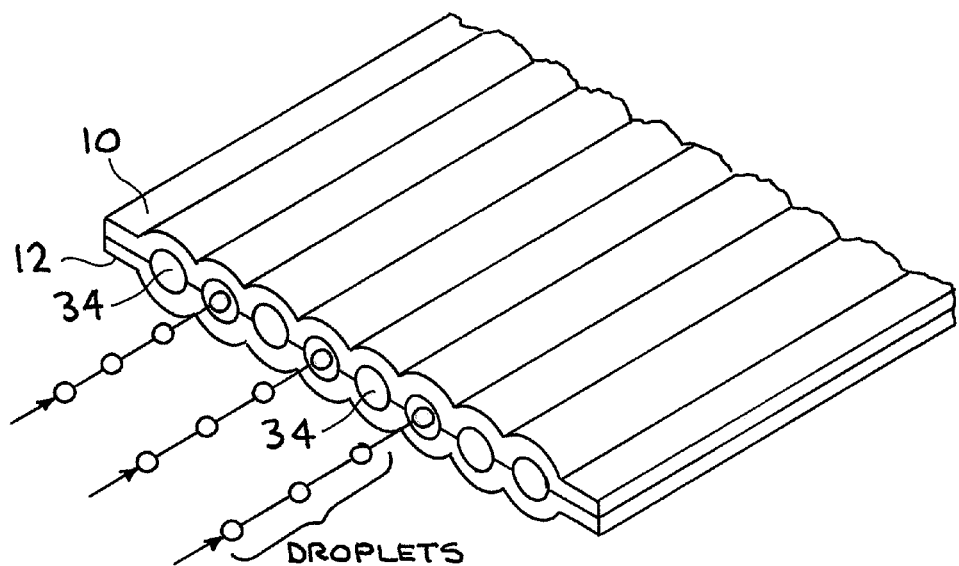
FIG. 17 illustrates an embodiment of the present invention providing a method of sealing fluid partitions using longitudinal cavities between the layers and creating microreactors by batch processing.

Referring now to FIGS. 16, 17, AND 18, additional embodiments of the present invention is illustrated providing a method of sealing fluid partitions using longitudinal cavities between the layers and creating micro-reactors by batch processing. The micro-reactors have sample or "packets" that range in size between milli-liters to pico-liters. In FIGS. 16, 17, AND 18 we show a MPBPS apparatus that uses the cavities between two polymeric sheets to produce sample filled micro-fluidic micro-reactors. As can be seen the two polymeric sheets 10 and 12 are positioned together and a longitudinal cavity 34 has been produced as has been previously explained. The sample can be introduced into the longitudinal cavity 34 by injection or the sample can be introduced into the longitudinal cavity 34 by the sampling wicking into the cavity by capillary action.

Referring now to FIG. 17, a dispenser 36 of the sample is positioned to dispense the sample between into the longitudinal cavity 34 between the ridges 14. As illustrated in FIG. 18A AND FIG. 18B, micro-reactors 38 of the sample can be produced by alternately introducing the sample and a fluid 36 into the cavity 34. For example, the micro-reactors 38 can be produced by the sample being in an aqueous micro-reactor 38 and the fluid 36 being oil or gas. In other embodiments of the invention the micro-reactors 38 of the sample can be produced by a droplet generator or microreactor maker positioned to direct micro-reactors containing the sample into the cavity 34. For example, a droplet generator as disclosed in U.S. Pat. RE 41,780, Chemical Amplification Based on Fluid Partitioning in an Immiscible Liquid can be positioned to direct droplets containing the sample into the cavity 34. In another example, a micro-reactor maker as disclosed in U. S. Published Patent Application No. 2009/0235990 for Monodisperse Microdroplet Generation and Stopping Without Coalescence published Sep. 24, 2009 can be positioned to direct microreactors containing the sample into the cavity 34. The disclosure of U. S. Published Patent Application No. 2009/0235990 for Monodisperse Microdroplet Generation and Stopping Without Coalescence is incorporated herein in its entirety for all purposes by this reference.

Figure 19:
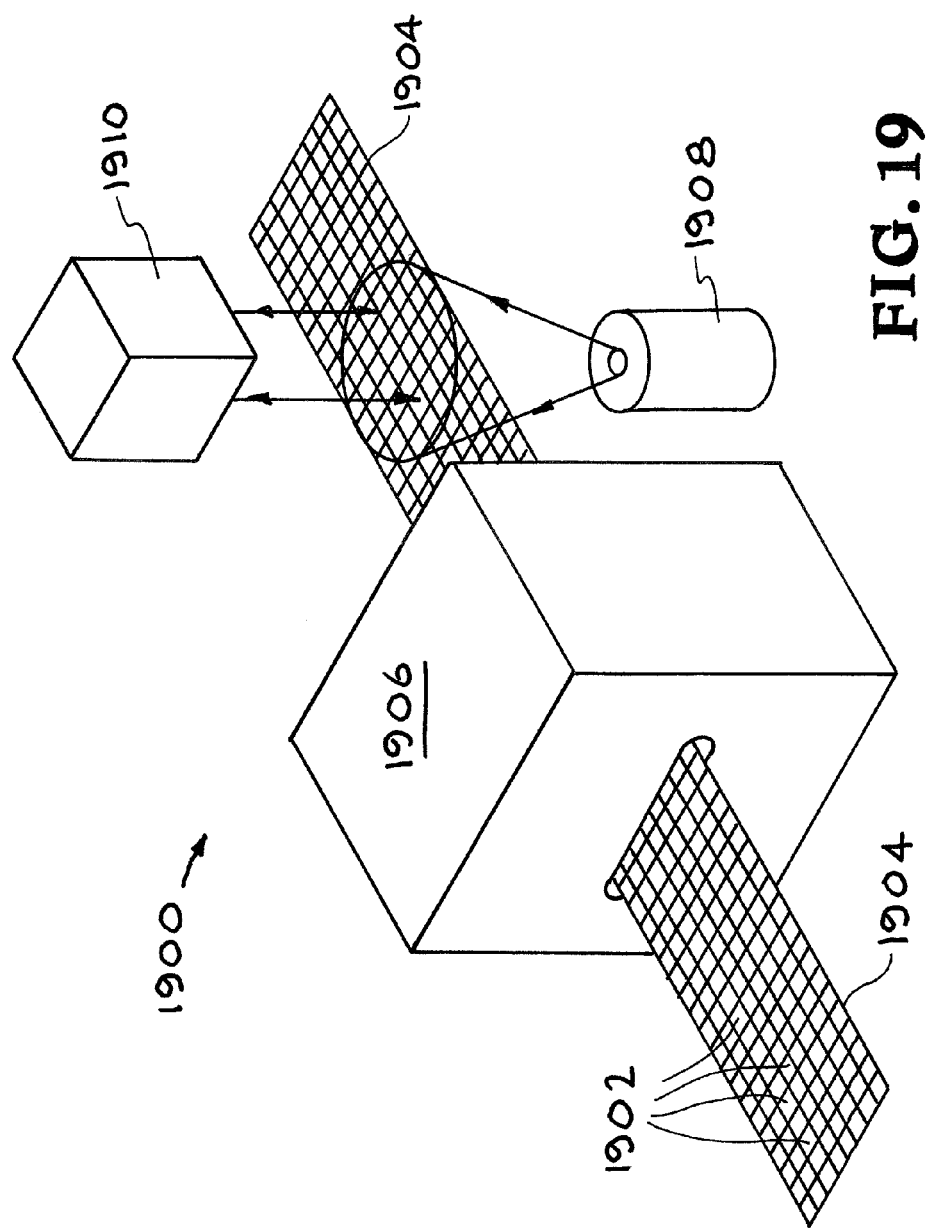
FIG. 19 illustrates an embodiment of the present invention for batch processing fluid partitioning for chemical amplification or other chemical processing or separations of a sample.

Referring now to FIG. 19, an embodiment of the present invention is illustrated that provides batch processing fluid partitioning for chemical amplification or other chemical processing or separations of a sample. The system illustrate in FIG. 19 is designated generally by the reference numeral 1900. The system 19 produces sample filled micro-fluidic micro-reactors 1902 on a batch strip 1904. The batch strip 1904 is fed into a thermal cycler 1906. The batch strip 1904 with the sample in the sample filled micro-fluidic micro-reactors 1902 emerges from the thermal cycler with the sample having been amplified. An interrogation system 1908 interrogates the amplified sample filled micro-fluidic micro-reactors 1902. The data acquisition system 1910 obtains, records, and stores information about the sample.

The system 1900 provides a method of batch processing fluid partitioning for chemical amplification or other chemical processing or separations of a sample. The method includes the steps of providing a first polymeric sheet for a first batch, providing a second polymeric sheet for the first batch, positioning the sample between the first polymeric sheet and the second polymeric sheet for the first batch, positioning the first polymeric sheet and the second polymeric sheet so they are parallel for the first batch, sealing the first polymeric sheet and the second polymeric sheet together thereby sealing the sample between the first polymeric sheet and the second polymeric sheet and partitioning the fluid for chemical amplification or other chemical processing or separations for the first batch, and processing the sample in a second batch.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for fluid partitioning for chemical amplification or other chemical processing or separations of a sample, comprising:
   a first dispenser of a first polymeric sheet;
   a second dispenser of a second polymeric sheet wherein said first dispenser and said second dispenser are positioned so that said first polymeric sheet and said second polymeric sheet become parallel;
   a dispenser of the sample positioned to dispense the sample between said first polymeric sheet and said second polymeric sheet; and
   a seal unit that seals said first polymeric sheet and said second polymeric sheet together thereby sealing the sample between said first polymeric sheet and said second polymeric sheet and partitioning the sample for chemical amplification or other chemical processing or separations, further comprising a chip for producing a magnetic field on said first polymeric sheet forming the sample into milli- to pico-liter-droplets oriented into a grid array.

2. The apparatus for fluid partitioning for chemical amplification or other chemical processing or separations of claim 1 further comprising a unit for coating said milli- to pico-liter-droplets with a monomer or dimer film.

3. The apparatus for fluid partitioning for chemical amplification or other chemical processing or separations of claim 2 further comprising a unit for curing said polymer film.

* * * * *